United States Patent
Kühnemund et al.

(10) Patent No.: US 12,270,071 B2
(45) Date of Patent: Apr. 8, 2025

(54) METHODS OF DETECTING AN ANALYTE

(71) Applicant: 10x Genomics, Inc., Pleasanton, CA (US)

(72) Inventors: Malte Kühnemund, Solna (SE); Toon Verheyen, Solna (SE)

(73) Assignee: 10X GENOMICS, INC., Pleasanton, CA (US)

( * ) Notice: Subject to any disclaimer, the term of this patent is extended or adjusted under 35 U.S.C. 154(b) by 190 days.

(21) Appl. No.: 17/127,455

(22) Filed: Dec. 18, 2020

(65) Prior Publication Data

US 2021/0198723 A1 Jul. 1, 2021

(30) Foreign Application Priority Data

Dec. 20, 2019 (GB) .................................... 1919032

(51) Int. Cl.
| | | |
|---|---|---|
| *C12P 19/34* | (2006.01) | |
| *C12Q 1/6816* | (2018.01) | |
| *C12Q 1/6876* | (2018.01) | |

(52) U.S. Cl.
CPC ......... *C12Q 1/6816* (2013.01); *C12Q 1/6876* (2013.01); *C12Q 2525/307* (2013.01); *C12Q 2531/125* (2013.01); *C12Q 2563/107* (2013.01)

(58) Field of Classification Search
USPC .......... 435/6.1, 6.11, 6.12, 91.1, 91.2, 91.51, 435/287.1, 287.2; 436/94, 501; 536/23.1, 24.3, 24.33, 25.3
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,883,867 A | 11/1989 | Lee |
| 4,965,188 A | 10/1990 | Mullis et al. |
| 5,321,130 A | 6/1994 | Yue et al. |
| 5,340,716 A | 8/1994 | Ullman et al. |
| 5,410,030 A | 4/1995 | Yue et al. |
| 5,436,134 A | 7/1995 | Haugland et al. |
| 5,512,462 A | 4/1996 | Cheng |
| 5,582,977 A | 12/1996 | Yue et al. |
| 5,635,352 A | 6/1997 | Urdea et al. |
| 5,658,751 A | 8/1997 | Yue et al. |

(Continued)

FOREIGN PATENT DOCUMENTS

| | | |
|---|---|---|
| EP | 1997909 | 12/2008 |
| EP | 2180062 | 4/2010 |

(Continued)

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.

(Continued)

*Primary Examiner* — Frank W Lu
(74) *Attorney, Agent, or Firm* — MORRISON & FOERSTER LLP

(57) ABSTRACT

In some aspects disclosed herein are methods and compositions for detecting a target nucleic acid molecule, said method comprising performing a linear oligo hybridization chain reaction (LO-HCR) to generate a polymeric product, and detecting the polymeric product, thereby detecting the target nucleic acid molecule.

13 Claims, 13 Drawing Sheets

(56) References Cited

U.S. PATENT DOCUMENTS

| | | |
|---|---|---|
| 5,695,940 A | 12/1997 | Drmanac et al. |
| 5,863,753 A | 1/1999 | Haugland et al. |
| 5,989,823 A | 11/1999 | Jayasena et al. |
| 6,117,635 A | 9/2000 | Nazarenko et al. |
| 6,248,526 B1 | 6/2001 | Weimer |
| 6,306,597 B1 | 10/2001 | Macevicz |
| 6,326,145 B1 | 12/2001 | Whitcombe et al. |
| 6,346,384 B1 | 2/2002 | Pollner |
| 6,534,266 B1 | 3/2003 | Singer |
| 7,255,994 B2 | 8/2007 | Lao |
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,632,641 B2 | 12/2009 | Dirks et al. |
| 7,655,898 B2 | 2/2010 | Miller |
| 7,721,721 B1 | 5/2010 | Kronengold et al. |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,198,031 B2 | 6/2012 | Chan-Yui et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2006/0234261 A1 | 10/2006 | Pierce et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0332368 A1 | 10/2020 | Ferree et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |

(56) References Cited

U.S. PATENT DOCUMENTS

| | | |
|---|---|---|
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Cher |
| 2023/0031305 A1 | 2/2023 | Neuta et al. |
| 2023/0031996 A1 | 2/2023 | Neuta et al. |
| 2023/0035685 A1 | 2/2023 | Neuta et al. |
| 2023/0037182 A1 | 2/2023 | Bava et al. |
| 2023/0039148 A1 | 2/2023 | Verheyen |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 1999/049079 | 9/1999 |
| WO | WO 2001/061037 | 8/2001 |
| WO | WO 2003/012119 | 7/2002 |
| WO | WO 2005/070630 | 8/2005 |
| WO | WO 2005/111236 | 11/2005 |
| WO | WO 2016/016450 | 2/2016 |
| WO | WO 2016/016452 | 2/2016 |
| WO | WO 2017/143155 | 8/2017 |
| WO | WO 2018/044939 | 3/2018 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123286 | 12/2020 |
| WO | WO 2021/123282 | 6/2021 |
| WO | WO 2021/138676 | 7/2021 |
| WO | WO 2021/155063 | 8/2021 |
| WO | WO 2021/168326 | 8/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Capodieci et al., "Gene expression profiling in single cells within tissue," Nat Methods. (2005) 2(9): 663-5.

Conze et al., "Single molecule analysis of combinatorial splicing," Nucleic Acids Res. (2010) 38(16): e163.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Maierhorfer et al., "Multicolor deconvolution microscopy of thick biological specimens," Am J Pathol. (2003) 162(2): 373-9.

Meade et al. "Multiplexed DNA detection using spectrally encoded porous SiO2 photonic crystal particles," Anal Chem. (2009) 81(7): 2618-25.

(56) References Cited

OTHER PUBLICATIONS

Sun et al., "Composite organic-inorganic nanoparticles as Raman labels for tissue analysis," Nano Lett. (2007) 7(2): 351-6.

Weibrecht et al., "Simultaneous visualization of both signaling cascade activity and end-point gene expression in single cells," PLoS One. (2011) 6(5): e20148.

Wilson et al., "Encoded microcarriers for high-throughput multiplexed detection," Angew Chem Int Ed Engl. (2006) 18;45(37): 6104-17.

Zhao et al., "Advances of multiplex and high throughput biomolecular detection technologies based on encoding microparticles," Sci China Chem. (2011) 54(8):1185.

Chemeris et al., "Real-time hybridization chain reaction," Dokl Biochem Biophys. (2008) 419: 53-55.

Choi et al., "Programmable in situ amplification for multiplexed imaging of mRNA expression," Nat Biotechnol. (2010) 28(11): 1208-1212.

Choi et al., "Third-generation in situ hybridization chain reaction: multiplexed, quantitative, sensitive, versatile, robust," Development. (2018) 6;145(12): dev165753.

Dirks et al., "Triggered amplification by hybridization chain reaction," Proc Natl Acad Sci U S A. (2004) 101(43): 15275-15278.

Duose et al., "Configuring robust DNA strand displacement reactions for in situ molecular analyses," Nucleic Acids Res. (2012) 40(7): 3289-3298.

Forcucci et al., "All-plastic miniature fluorescence microscope for point-of-care readout of bead-based bioassays," J Biomed Opt. (2015) 20(10): 105010.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Heid et al., "Real time quantitative PCR," Genome Res. (1996) 6(10): 986-94.

Holland et al., "Detection of specific polymerase chain reaction product by utilizing the 5'—3' exonuclease activity of Thermus aquaticus DNA polymerase," Proc Natl Acad Sci U S A. (1991) 88(16): 7276-7280.

Lee et al., "Allelic discrimination by nick-translation PCR with fluorogenic probes," Nucleic Acids Res. (1993) 21(16): 3761-3766.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

McGinn et al., "New technologies for DNA analysis—a review of the READNA Project," N Biotechnol. (2016) 33(3): 311-30. doi: 10.1016/j.nbt.2015.10.003.

Nazarenko et al., "A closed tube format for amplification and detection of DNA based on energy transfer," Nucleic Acids Res. (1997) 25(12): 2516-21.

Niu et al., "Fluorescence detection for DNA using hybridization chain reaction with enzyme-amplification," Chem Commun (Camb). (2010) 46(18): 3089-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Ravan, "Isothermal RNA detection through the formation of DNA concatemers containing HRP-mimicking DNAzymes on the surface of gold nanoparticles," Biosens Bioelectron. (2016) 80: 67-73.

Rouhanifard et al. "ClampFISH detects individual nucleic acid molecules using click chemistry-based amplification," Nat Biotechnol. (2018) 17 pages. doi: 10.1038/nbt.4286.

Shah et al., "In situ transcription profiling of single cells reveals spatial organization of cells in the mouse hippocampus," Neuron. (2016) 92(2): 342-357.

Song et al., "Hybridization chain reaction-based aptameric system for the highly selective and sensitive detection of protein," Analyst. (2012) 137(6):1396-1401.

Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.

Tyagi et al., "Molecular Beacons: Probes that Fouresce upon Hybridization," Nature Biotechnology. (1996) 14:303-308.

Wählby et al., "Sequential immunofluorescence staining and image analysis for detection of large numbers of antigens in individual cell nuclein," Cytometry. (2002) 47(1): 32-41.

Whitcombe et al., "Detection of PCR products using self-probing amplicons and fluorescence," Nat Biotechnol. (1999) 17(8): 804-807.

Wu, C. et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.

Xiao et al., "Single-Cell in Situ RNA Analysis With Switchable Fluorescent Oligonucleotides," Front Cell Dev Biol. (2018) 6:42.

METHODS OF DETECTING AN ANALYTE

CROSS-REFERENCE TO RELATED APPLICATIONS

This application claims priority to Great Britain Patent Application No. GB1919032.1, filed Dec. 20, 2019, which application is herein incorporated by reference in its entirety for all purposes.

FIELD

The present disclosure generally relates to methods and compositions for the detection of a target analyte in a sample.

BACKGROUND

Single molecule fluorescent in situ hybridization (smFISH), including amplified smFISH methods such as hybridisation chain reaction (HCR), are widely used techniques utilized to determine expression levels of analytes, such as RNA. A major limitation of these approaches are that the signals may be dim while background fluorescence may be concomitantly high (especially in samples such as FFPE samples) with large variability depending on the tissue type, sample age, and fixation conditions. Imaging at high magnification (e.g., 60×-100×) is usually required. As a result, only a very small area of the sample is usually imaged (typically, 40-50 fields of view), thus limiting the ability to detect target analyte variability across a sample. Thus, improved methods are needed. The present disclosure addresses this and other needs.

SUMMARY

In some embodiments, provided herein is a method of detecting an analyte in a sample. In some embodiments, the method comprises: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte.

In some embodiments, performing the linear oligo hybridization chain reaction comprises contacting the target nucleic acid molecule with the initiator to provide the initiator hybridized to the target nucleic acid molecule.

In any of the preceding embodiments, the first species and/or the second species may not comprise a hairpin structure.

In any of the preceding embodiments, the plurality of LO-HCR monomers may not comprise a metastable secondary structure.

In any of the preceding embodiments, the plurality of LO-HCR monomers may not comprise a repeating sequence of more than about 5, about 10, or about 20 nucleotides in length.

In any of the preceding embodiments, the LO-HCR polymer may not comprise a branched structure.

In any of the preceding embodiments, the LO-HCR monomers can be between about 10 and about 100 nucleotides in length.

In any of the preceding embodiments, an LO-HCR monomer of the first species can hybridize to an LO-HCR monomer of the second species, which in turn can hybridize to an LO-HCR monomer of the first species.

In any of the preceding embodiments, an LO-HCR monomer of the first species can hybridize to an LO-HCR monomer of the second species, which in turn can hybridize to an LO-HCR monomer of a third species, which in turn can hybridize to an LO-HCR monomer of a fourth species, which in turn can hybridize to an LO-HCR monomer of the first species.

In any of the preceding embodiments, the analyte can be a cellular nucleic acid molecule and the target nucleic acid molecule can be the cellular nucleic acid molecule or a nucleic acid molecule generated from the cellular nucleic acid molecule. In some embodiments, the target nucleic acid molecule comprises a reporter comprising a marker sequence indicative of said cellular nucleic acid molecule. In some embodiments, the initiator hybridizes directly or indirectly to or is comprised in the marker sequence.

In any of the preceding embodiments, the cellular nucleic acid molecule can be a DNA or a RNA molecule, including gDNA, mRNA, miRNA, lncRNA.

In any of the preceding embodiments, the nucleic acid molecule can be a cDNA molecule generated from the cellular nucleic acid molecule, an amplified product comprising a sequence of said cellular nucleic acid molecule, or a nucleic acid probe or component of a probe that targets said cellular nucleic acid molecule.

In any of the preceding embodiments, the analyte can be a non-nucleic acid analyte, optionally a lipid or a protein, and the target nucleic acid molecule can comprise a reporter comprising a marker sequence indicative of said non-nucleic acid analyte.

In any of the preceding embodiments, the sample can comprise cells, wherein optionally the cells are immobilized, fixed or in suspension.

In any of the preceding embodiments, the analyte can be detected in situ in a tissue sample, optionally in single cells.

In any of the preceding embodiments, the method can be used to detect multiple target analytes in a sample, and at least one target nucleic acid molecule can be provided for each target analyte. In some embodiments, multiple polymeric products are generated for each target analyte.

In any of the preceding embodiments, the target nucleic acid molecule can comprise multiple copies of the marker sequence, such that multiple LO-HCR reactions can be initiated from each target nucleic acid molecule, and/or multiple target nucleic acid molecules may be provided for each target analyte.

In any of the preceding embodiments, the target nucleic acid molecule can be a hybridization probe which is capable of hybridizing to the analyte. In some embodiments, the hybridization probe comprises a target binding domain, which is capable of hybridizing to the target analyte, and an initiator binding domain which comprises at least one copy of a marker sequence indicative of said analyte.

In any of the preceding embodiments, the target nucleic acid molecule can be a ligatable probe provided in one or more parts, including a padlock probe or a probe comprising multiple component parts which are capable of hybridizing to a target analyte such that they can be ligated together.

In any of the preceding embodiments, the target nucleic acid molecule can be a rolling circle amplification product (RCP) generated from the analyte or from a reporter for the target analyte.

In any of the preceding embodiments, the initiator can be provided in two or more parts.

In any of the preceding embodiments, the initiator can be in the form of an initiator complex which is capable of supporting multiple LO-HCR reactions, such that multiple LO-HCR reactions can be initiated from each marker sequence.

In any of the preceding embodiments, performing the LO-HCR reaction can comprise: (a) contacting the target nucleic acid molecule with the initiator to provide the initiator hybridized to the target nucleic acid molecule, wherein the initiator comprising an output domain complementary to the first hybridization region of the first species LO-HCR monomer; (b) hybridizing the first species of LO-HCR monomer to the initiator, wherein the first species optionally comprises a detectable label; (c) hybridizing the second species of LO-HCR monomer to the second hybridization region of the first species of LO-HCR monomer, wherein the second species optionally comprises a detectable label; and (d) repeating steps (b) to (c) one or more times to generate a detectable polymeric LO-HCR product.

In any of the preceding embodiments, performing the LO-HCR reaction can comprise a step of contacting the target nucleic acid molecule simultaneously with the at least first and second species of LO-HCR monomers.

In any of the preceding embodiments, wherein at least a fraction of the plurality of LO-HCR monomers in the LO-HCR reaction can be labelled with a detectable label, optionally the first species of LO-HCR monomer can be provided with a detectable label. In some embodiments, the detectable label is a fluorescent label.

In any of the preceding embodiments, the first and/or second species of LO-HCR monomers can comprise an overhang region capable of facilitating a displacement reaction to depolymerize the polymeric product.

In any of the preceding embodiments, for each target nucleic acid molecule, multiple sequential LO-HCR reactions can be performed, and wherein detection of the analyte can comprise detection of signals from the multiple sequential LO-HCR reactions. In some embodiments, sequential LO-HCR reactions are performed using differentially labelled LO-HCR monomer sets, such that each target nucleic acid molecule is combinatorially labelled to detect the analyte.

In some embodiments, provided herein is a kit for detecting a nucleic acid or non-nucleic acid target analyte in a sample, said kit comprising: (i) a set of LO-HCR monomers for assembly into an LO-HCR product comprising at least first and second LO-HCR monomers, wherein the first LO-HCR monomers have an input domain complementary to the initiator domain of an initiator and the output domain of the second LO-HCR monomer, and an output domain complementary to the input domain of the second LO-HCR monomer; and wherein the second LO-HCR monomers have an input domain complementary to the output domain of the first LO-HCR monomer and an output domain complementary to the input domain of the first or a subsequent LO-HCR monomer, said LO-HCR monomers being capable of being hybridized together to form an LO-HCR product, wherein said LO-HCR monomers each is a single-stranded linear oligonucleotide having no metastable secondary structure.

In some embodiments, said kit further comprises one or more of: (ii) a nucleic acid probe for detecting a target analyte, wherein the probe comprises a marker sequence indicative of said analyte; (iii) an HCR initiator in one or more parts which is capable of hybridizing to a marker sequence in the probe or in the target analyte; and/or (iv) reagents for performing an RCA reaction. In some embodiments, the nucleic acid probe is a circular or circularizable nucleic acid molecule.

DETAILED DESCRIPTION

Figure 1:
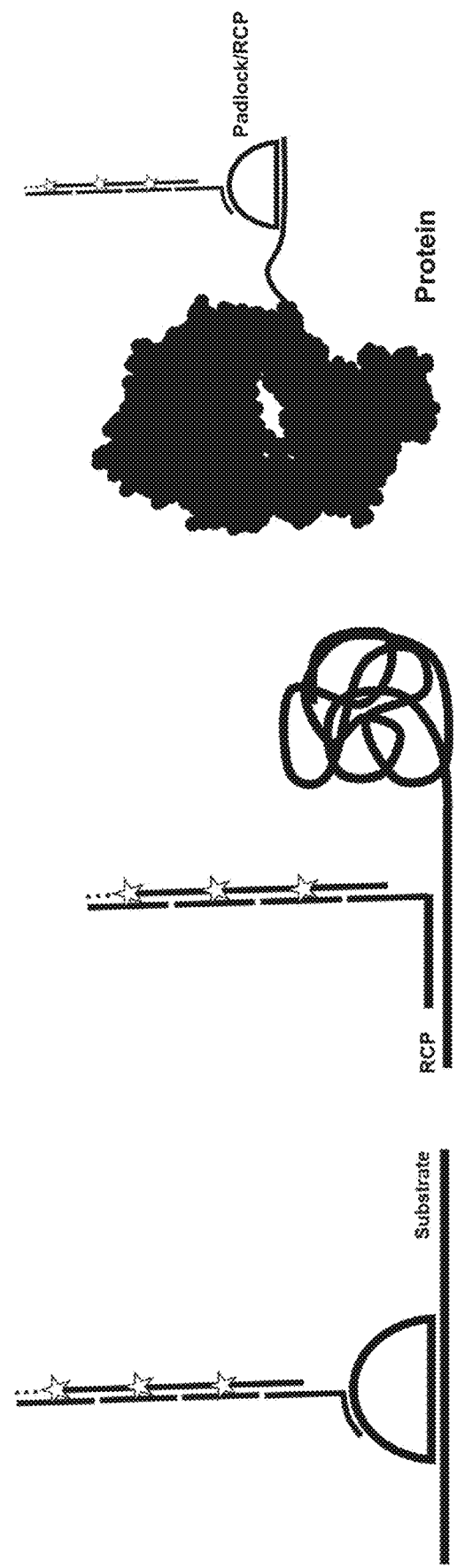
FIG. 1 shows exemplary target nucleic acid molecules with HCR initiators hybridized thereto and labeled HCR polymeric products generated from LO-HCR monomers.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

In some embodiments, the present disclosure relates to the detection of a target analyte in a sample by a method comprising a chain reaction of hybridization events among linear oligonucleotides, e.g., linear oligos with no hairpin or other metastable secondary structure. In some embodiments, the method, termed herein "linear oligo hybridization chain reaction" (LO-HCR), involves detecting a nucleic acid or non-nucleic acid target analyte by detecting the polymeric product of an LO-HCR reaction which acts as a reporter for the target analyte, wherein the LO-HCR reaction is conducted using LO-HCR monomers which, contrary to conventional and known hybridization chain reaction (HCR) monomers, have a single-stranded linear structure with no hairpin or other metastable secondary structure.

Many analyte-detection methods typically involve the detection of fluorescent signals, including particularly for the detection of analytes in situ in the tissues in which they are located. This includes proteins, lipids and other molecules, including nucleic acids, which it is frequently desirable to detect at the single molecule level. Techniques for quantifying single molecule nucleic acid targets known in the art are generally applicable to tissue samples which have low autofluorescence. However, most human tissue samples, including brain and the vast majority of cancer tissue samples, exhibit high autofluorescence, which makes single molecule quantification difficult. This can also apply to the detection of protein analytes using fluorescently labelled probes or reporter molecules.

Single molecule fluorescent in situ hybridization (smFISH) is a widely used technique to determine expression levels by detecting mRNA. In smFISH, a set of typically 30-50 oligonucleotides, each about 20 nucleotides in length and each directly conjugated to a single fluorophore, are first hybridized to a complementary mRNA target. Individual transcripts are then visualized as diffraction-limited spots using wide-field epifluorescence microscopy, and quantified (Raj et al, 2008, Nat Methods, 5, 877-879). Alternatively, smFISH probes may carry, instead of a directly conjugated fluorescent label, a 10-30 nucleotide long overhang sequence, which is not hybridized to the mRNA target, and that can be detected by hybridization thereto of fluorescently conjugated detection probes.

The smFISH technique has been used to quantify the expression and topographic distribution of two prominent breast cancer biomarkers and drug targets, epidermal growth factor receptor 2 (HER2) and estrogen receptor 1 (ER) in formalin-fixed, paraffin-embedded (FFPE) tissue samples. In another study, smFISH was used on mouse brain sections to quantify gene expression of cell type specific marker genes. In order to analyze several marker genes in the same tissue section, smFISH was performed sequentially by first adding a set of smFISH probes for 3 genes, each labelled with a different fluorescent reporter, and then fluorescently imaging the smFISH signals, removing the smFISH probes or the fluorescent labels and then hybridizing a different set of smFISH probes or probe labels for 3 other genes and imaging the smFISH signals. A major limitation of this approach, however, is that the smFISH signals are dim while background fluorescence is high in FFPE samples (with large variability depending on the tissue type, sample age, and fixation conditions).

Hence, imaging at high magnification (60×-100×) is required. As a result, only a very small area of the sample is usually imaged (typically, 40-50 fields of view), thus limiting the ability to detect target analyte variability across a sample. This presents a disadvantage for analysis in cases where there can be a heterogeneity in the presence of the target analyte between different cells or regions of the tissue, for example in tumours, where it is becoming apparent that most cancer types harbour a high degree of intra-tumour heterogeneity and that the spatial distribution of cells expressing a biomarker might also represent a prognostic or predictive factor. It is therefore desirable to develop methods which are able not only to quantitatively determine the expression of a target analyte in a sample, and therefore provide a measure of its abundance, but which can also reflect the spatial distribution and heterogeneity of the target analyte inside the sample.

In order to enable faster imaging, and to improve detection efficiency and specificity in autofluorescent tissues, the signals from fluorescent probes need to be further amplified. For signal amplification, an HCR reaction is a very useful technique that allows digital quantification of individual nucleic acid molecules with a detection sensitivity comparable to other methods, and with increased imaging throughput.

HCR is known in the art as a technique for enzyme-free nucleic acid amplification based on a triggered chain of hybridization of monomer nucleic acid molecules (termed "HCR monomers") to one another to form a nicked nucleic acid polymer. This polymeric product of the HCR reaction may be generated as a signal which is ultimately detected in order to indicate the presence of a target analyte. In other words, HCR may be used as a signal-generating means to generate a readily detectable signal for detection of a target analyte.

HCR was initially described in Dirks and Pierce, 2004, PNAS, 101(43), 15275-15278 and in U.S. Pat. Nos. 7,632, 641 and 7,721,721 and has subsequently been developed as a detection technique (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR has previously been combined with smFISH and tissue clearing to increase signal to noise ratio (SNR) in mouse brain samples (Shah et al 2016, Neuron. 92(2):342-357. doi:10.1016/j.neuron.2016.10.001).

HCR monomers known in the art comprise a hairpin, or other metastable nucleic acid structure, such that they are not able to hybridize to one another until the opening of a monomer is triggered by a so-called HCR initiator, which hybridizes to a HCR monomer and invades its structure, allowing it open and become available to hybridize to another HCR monomer, and so on, in a chain reaction.

In the simplest form of HCR, two different types of stable hairpin monomer, referred to here as first and second HCR monomers, undergo a chain reaction of hybridization events to form a long nicked double-stranded DNA molecule when an HCR initiator nucleic acid molecule is introduced. The HCR monomers have or comprise a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure are known as the "toehold region" (or "input domain"). The first HCR monomers each further comprise a sequence which is complementary to a sequence in the exposed toehold region of the second HCR monomers. This sequence of complementarity in the first HCR monomers is known as the "interacting region" (or "output domain"). Similarly, the second HCR monomers each comprise an interacting region (output domain), i.e. a sequence which is complementary to the exposed toehold region (input domain) of the first HCR monomers.

Crucially, however, in the absence of the HCR initiator, these interacting regions are protected by the secondary structure (i.e. they are not exposed), and thus the hairpin monomers are stable or kinetically trapped (also referred to as "metastable"), and remain as monomers (i.e. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (i.e. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted, leading to the formation of a nicked chain of alternating units of the first and second monomer species.

A fundamental principle behind HCR as described in the art is thus that short loops of nucleic acid are resistant to invasion by complementary single stranded nucleic acids. This stability allows for the storage of potential energy in the form of nucleic acid loops. Potential energy is released when a triggered conformational change allows the single stranded bases which were present in the loops to hybridize with a complementary strand. The HCR monomers thus contain such a loop, as well as a region of complementarity to another HCR monomer which is shielded or protected by the loop structure, such that it can only hybridize to the other HCR monomer when the loop structure is opened up.

It has up to now been believed that it is necessary, in order to achieve an acceptable signal to noise ratio, to control the HCR reaction by using metastable HCR monomers which are not able to hybridize to one another until the HCR reaction is triggered by the HCR initiator. However, the present inventors have surprisingly found that, in fact, a chain reaction of hybridization events can be conducted with monomers having a single-stranded linear structure, e.g., without a metastable secondary structure that traps the interacting region of a monomer for hybridization to another monomer or an initiator, and that an acceptable signal to noise ratio can be achieved in the detection of target analytes using such a modified HCR readout, despite the possibility of non-specific chain reactions occurring. In particular, it has been found that by providing multiple initiation points for the chain reaction of hybridization events (i.e. a "concentration" of initiators), such that multiple chain reaction products may be associated with a target analyte, the signal from the analyte may be distinguished from any non-specific signals. Further, by forming the chain reaction products on an immobilized target nucleic acid molecule, and washing away any non-specific chain reaction products, an efficient assay may be achieved. However, such assay formats are not essential, and it is possible to detect and distinguish single target analyte-specific chain reaction products from background or non-specific signal, and thereby detect a target analyte using this method, particularly by microscopy-based detection methods.

Accordingly, therefore, the present inventors have developed a beneficial new detection method for the detection of target analytes which is efficient, robust and more flexible, and may readily be performed using simplified chain reaction reagents. The increased flexibility associated with the new LO-HCR method, relative to known HCR methods involving the use of hairpin monomers is achieved as the design of the chain reaction monomers is far less restricted for linear monomers than for hairpin HCR monomers, which need to be optimized for every set of two hairpin monomers. Although of particular benefit for the localized detection of single nucleic acid molecules in tissue samples, including notably RNA, the method is of more general applicability, and provides an improved method of detecting, in any sample, any analyte molecule which may be detected by an assay involving the generation of a target nucleic acid molecule, i.e. any assay which uses a nucleic acid probe or reporter molecule. This includes protein or other non-nucleic acid analytes which are detected by an assay method or probe which uses or generates a nucleic acid molecule as a reporter for the analyte.

Throughout the present disclosure, the terms HCR, HCR monomer, HCR initiator, HCR product, HCR reaction, HCR signal, etc. are sometimes used in connection with describing aspects of LO-HCR. It should be appreciated that use of such HCR terminology does not equate or limit embodiments of the present disclosure to hairpin-mediated HCR methods or aspects thereof.

Accordingly, in some embodiments, the present disclosure, and the present invention, provides a method of detecting a nucleic acid or non-nucleic acid target analyte in a sample, wherein said analyte is detected by detecting a target nucleic acid molecule, said method comprising: (i) providing a target nucleic acid molecule which is a target nucleic acid analyte or a part thereof, or which has been generated from a target nucleic acid analyte or as a reporter for a nucleic acid or non-nucleic acid target analyte, and which comprises at least one copy of a marker sequence indicative of said analyte; (ii) performing a hybridization chain reaction (HCR) using at least two species of HCR monomers to generate a polymeric HCR product, wherein said HCR reaction is initiated by an HCR initiator which is provided in one or more parts and which hybridizes to said marker sequence or is comprised in said marker sequence; (iii) detecting the polymeric HCR product, thereby to detect the target analyte; wherein the HCR monomers each have a single-stranded linear structure.

In any of the preceding embodiments, the target analyte can comprise a nucleic acid molecule, a lipid, and/or a protein.

In any of the preceding embodiments, the nucleic acid molecule can be DNA or RNA, including gDNA, cDNA, mRNA, miRNA, lncRNA or a nucleic acid probe or component of a probe or an amplification product thereof.

In any of the preceding embodiments, the sample may comprise cells. In some embodiments, the cells are immobilized, fixed or in suspension.

In any of the preceding embodiments, the target analyte can be detected in situ in a tissue sample, optionally in single cells.

In any of the preceding embodiments, the method can be used to detect multiple target analytes in a sample, and at least one target nucleic acid molecule is provided for each target analyte.

In any of the preceding embodiments, the step (ii) of performing an HCR reaction involves generating multiple HCR products for each target analyte.

In any of the preceding embodiments, the target nucleic acid molecule can comprise multiple copies of the marker sequence, such that multiple HCR reactions can be initiated from each target nucleic acid molecule, and/or wherein multiple target nucleic acid molecules are provided for each target analyte.

In any of the preceding embodiments, the target nucleic acid molecule can comprise a hybridization probe which is capable of hybridizing to the target analyte or to a probe or a part thereof for the target analyte. In some embodiments, the hybridization probe comprises a target binding domain, which is capable of hybridizing to the target analyte, and an initiator binding domain which comprises at least one copy of a marker sequence indicative of said analyte.

In any of the preceding embodiments, the target nucleic acid molecule can comprise a ligatable probe provided in one or more parts, including a padlock probe or a probe comprising multiple component parts which are capable of hybridizing to the target analyte such that they can be ligated together.

In any of the preceding embodiments, the target nucleic acid molecule can be a rolling circle amplification product (RCP) generated from the target analyte or as a reporter for the target analyte.

In any of the preceding embodiments, the HCR initiator can be provided in two or more parts.

In any of the preceding embodiments, the HCR initiator can be in the form of an initiator complex which is capable of supporting multiple HCR reactions, such that multiple HCR reactions can be initiated from each marker sequence.

In any of the preceding embodiments, the step (ii) of performing an HCR reaction can comprises: (a) contacting the target nucleic acid molecule with an HCR initiator having an output domain complementary to the input domain of a first HCR monomer; (b) contacting the target nucleic acid molecule with first HCR monomers having an input domain complementary to the initiator output domain and an output domain complementary to the input domain of a second HCR monomer; (c) optionally washing the target nucleic acid molecule; (d) contacting the target nucleic acid molecule with second HCR monomers having an input domain complementary to the output domain of the first HCR monomer and an output domain complementary to the input domain of the first HCR monomer; (e) optionally washing the target nucleic acid molecule; and (f) repeating steps (b) to (e) until a detectable HCR product has been generated.

In any of the preceding embodiments, the step (ii) of performing an HCR reaction can comprise a step of contacting the target nucleic acid molecule simultaneously with at least two different species of HCR monomers. In any of the preceding embodiments, at least a fraction of the HCR monomers in an HCR reaction can be labelled with a detectable label, optionally wherein the first HCR monomer is provided with a detectable label. In some embodiments, the detectable label can be a fluorescent label.

In any of the preceding embodiments, first and/or second HCR monomers can comprise an overhang region capable of facilitating a displacement reaction to depolymerize the HCR product.

In any of the preceding embodiments, for each target nucleic acid molecule, multiple sequential HCR reactions can be performed, and the respective HCR products may be detected together to provide for detection of the analyte. In some embodiments, sequential HCR reactions are performed using differentially labelled HCR monomer sets, such that each target nucleic acid molecule is combinatorially labelled to detect the analyte.

In some embodiments, provided herein is a kit for detecting a nucleic acid or non-nucleic acid target analyte in a sample, said kit comprising: (i) means for performing a HCR reaction comprising a set of HCR monomers for assembly into an HCR product comprising at least first and second HCR monomers, wherein the first HCR monomers have an input domain complementary to the initiator domain of an HCR initiator and the output domain of the second HCR monomer, and an output domain complementary to the input domain of the second HCR monomer; and wherein the second HCR monomers have an input domain complementary to the output domain of the first HCR monomer and an output domain complementary to the input domain of the first or a subsequent HCR monomer, said HCR monomers being capable of being hybridized together to form a HCR product, wherein said HCR monomers each have a single-stranded linear structure.

In some embodiments, the kit further comprises one or more of: (ii) a nucleic acid probe for detecting a target analyte, wherein the probe comprises a marker sequence indicative of said analyte; (iii) an HCR initiator in one or more parts which is capable of hybridizing to a marker sequence in the probe or in the target analyte; and/or (iv) means for performing an RCA reaction.

In any of the preceding embodiments, the nucleic acid probe can comprise a circular or circularizable nucleic acid molecule.

In any of the preceding embodiments, the initiator can be contacted with LO-HCR monomers of at least a first and a second species to generate a polymeric product, wherein the first species comprises a first hybridization region which is linear, single-stranded, and in a non-loop region of the first species prior to generating the polymeric product, the second species comprises a second hybridization region which is linear, single-stranded, and in a non-loop region of the second species prior to generating the polymeric product, and the first and second hybridization regions are complementary to each other.

In any of the preceding embodiments, the initiator can be provided in one or more parts, and can hybridize directly or indirectly to or can be comprised in the target nucleic acid molecule.

In any of the preceding embodiments, the first and second hybridization regions may be partially or entirely outside a secondary structure of the first and second species, respectively, optionally wherein the secondary structure is a metastable secondary structure. In some embodiments, the secondary structure is a hairpin structure.

In any of the preceding embodiments, each LO-HCR monomer can be a single-stranded linear oligonucleotide having no metastable secondary structure.

In any of the preceding embodiments, one or more LO-HCR monomers may not comprise a repeating sequence of more than about 5, about 10, or about 20 nucleotides in length. In some embodiments, none of the LO-HCR monomers comprises a repeating sequence of between about 10 and about 30 nucleotides in length.

In any of the preceding embodiments, the LO-HCR monomers can be between about 10 and about 100 nucleotides in length.

In any of the preceding embodiments, an LO-HCR monomer of the first species can hybridize to an LO-HCR monomer of the second species, which in turn can hybridize to an LO-HCR monomer of the first species.

In any of the preceding embodiments, an LO-HCR monomer of the first species can hybridize to an LO-HCR monomer of the second species, which in turn can hybridize to an LO-HCR monomer of a third species, which in turn can hybridize to an LO-HCR monomer of a fourth species, which in turn can hybridize to an LO-HCR monomer of the first species.

In a further aspect, there is provided a kit for detecting a nucleic acid or non-nucleic acid target analyte in a sample, said kit comprising: (i) means for performing a HCR reaction comprising a set of HCR monomers for assembly into an HCR product, said set comprising at least first and second HCR monomers, wherein the first HCR monomers have an input domain complementary to the initiator domain of an HCR initiator and the output domain of the second HCR monomer, and an output domain complementary to the input domain of the second HCR monomer; and wherein the second HCR monomers have an input domain complementary to the output domain of the first HCR monomer and an output domain complementary to the input domain of the first or a subsequent HCR monomer, said HCR monomers being capable of being hybridized together to form a HCR product, wherein said HCR monomers each have a single-stranded linear structure and are LO-HCR monomers; (ii) a nucleic acid probe for detecting a target analyte, wherein the probe comprises a marker sequence indicative of said analyte; (iii) an HCR initiator in one or more parts which is capable of hybridizing to a marker sequence in the probe or in the target analyte; and/or (iv) means for performing a rolling circle amplification (RCA) reaction, e.g. a polymerase enzyme, for example a strand-displacing polymerase, e.g. Phi29 polymerase, and/or a primer for a RCA reaction.

Advantageously, and as described further below, in the present method, the step of performing a HCR reaction may comprise generating multiple HCR products for each analyte. In particular, multiple HCR products may be generated for the analyte in one HCR reaction, that is in one run or cycle of the HCR reaction which is performed. This may be achieved by providing a target nucleic acid molecule comprising multiple (i.e. at least two) copies of a marker sequence, and/or multiple target molecules for each analyte, and/or a HCR initiator capable of initiating multiple HCR reactions (i.e. multiple separate HCR reactions per HCR initiator). In other words, the method may comprise providing at least two marker sequences per target nucleic acid molecule (or in other words, the target nucleic acid molecule may comprise at least 2 copies of a marker sequence), and/or at least two target nucleic acid molecules for a target analyte to be detected, and/or initiating at least two HCR reactions from each HCR initiator. In the case of the latter, the HCR initiator may comprise at least two HCR initiation points (or initiation sites), i.e. at least two initiator domains.

Analogously, in an embodiment, the kit comprises at least two nucleic acid probes, and/or the nucleic acid probe comprises at least two copies of the marker sequence, and/or the HCR initiator comprise at least two initiation domains (i.e. is capable of initiating at least two HCR reactions (more particularly, at least two separate HCR reactions).

In the HCR reaction, HCR monomers are polymerised to form a HCR product (HCR polymer) by hybridization to one another. In particular, a set of HCR monomers designed to hybridize to one another (for example a set of first and second HCR monomers) are polymerised to form a HCR product. The initiator binds to a first HCR monomer, leading it to bind to second HCR monomer, which in turn binds to another first HCR monomer, and so on in a cascade reaction. This is described further below. HCR monomers designed to hybridize to one another to form a HCR product may be termed as "cognate" HCR monomers or as a HCR monomer set, or HCR monomer system. As noted above, unlike conventional HCR monomers, which comprise a hairpin or other metastable nucleic acid structure, the present method uses HCR monomers which each have a single-stranded linear structure, i.e. which have no secondary structure. In particular, the HCR monomers have no regions of self-complementarity which are capable of forming an intramolecular duplex. In other words, the HCR monomers do not comprise any double-stranded regions, and in particular do not have, contain or comprise any intra-molecular double-stranded region. They do not have any hairpin or stem-loop structure(s). The HCR monomers are single-stranded linear oligonucleotides comprising no regions of duplex, or more particularly no stem-loop structure.

An HCR monomer set may be specific to, or cognate for, a particular HCR initiator sequence, such that the HCR reaction involving that set may be triggered (or initiated) only by a particular HCR initiator. The HCR initiator is provided in one or more parts and may be comprised in the marker sequence in the target nucleic acid molecule, or may hybridize to the marker sequence in the target nucleic acid molecule. Accordingly, the initiation of the HCR reaction is dependent on the presence of the target nucleic acid molecule, and is determined by the marker sequence that is present in the target nucleic acid molecule. In turn, the presence of the target molecule is dependent on the presence and/or amount of the target analyte, or is indicative of the presence and/or amount of the target analyte.

In an embodiment, the HCR monomers for the HCR reaction may be selected or designed so as to generate a HCR product which is distinctive, or indicative, for the analyte. In an embodiment, the HCR product generated for a given analyte may thus be distinguished from a HCR product generated for another analyte. In another embodiment, multiple HCR products may be generated based on the target nucleic acid molecule for a given analyte, and together the multiple HCR products may provide the signal by means of which an analyte is detected, and distinguished. For example, multiple HCR products may be generated in a combinatorial or sequential labelling scheme, as described further below. Thus, for a given analyte, multiple sets of HCR monomers may be provided, each for a separate HCR reaction. (Each set may comprise the monomers necessary for producing a HCR product, e.g. comprising 2 species of HCR monomers cognate for one another, that is which hybridize together to form a HCR product, and different sets may produce distinct, or distinguishable, HCR products). Alternatively or additionally, multiple sets of HCR monomers may be provided for multiplex detection of multiple different analytes, wherein for each analyte a different set, or different sets, of HCR monomers are provided. Such multiplex methods for detecting multiple analytes may be performed in cycles, and are discussed further below.

The target analyte to be detected by the methods herein may be any analyte which it is desired to detect. It may thus be any substance, molecule or entity it is desired to detect. The method herein relies upon the detection of a target nucleic acid molecule in order to detect the analyte. The target nucleic acid molecule may be the target analyte, or a part thereof, where the target analyte is a nucleic acid, or it may be provided or generated as a proxy, or a marker, for the target analyte. The target nucleic acid molecule determines the signal which is detected, and thus acts as a reporter for (i.e. is indicative of) the target analyte.

As will be described in more detail below, the target nucleic acid molecule may be a hybridization probe which is capable of hybridizing to the target analyte, or to a probe (or a part thereof) for the target analyte. Alternatively, the target nucleic acid molecule may be an amplification product (amplicon) or complementary copy of a target analyte, or of a probe for a target analyte or a part or component of such a probe. For example, it may be a rolling circle amplification product (RCP) generated from the target analyte, or as a reporter for the target analyte.

The term "reporter" is thus used broadly herein to denote a molecule which is used to report on the presence or absence of the analyte—it is a molecule which is detected in the assay method in order to detect the analyte, or which is used or generated as part of the signal generating system to detect the analyte. In the present methods, the reporter is a nucleic acid molecule which is detected as a marker (or proxy or indicator) of the presence of the analyte.

The analyte is the ultimate target of the detection method and may accordingly be any biomolecule or chemical compound, including a protein or peptide, or a nucleic acid molecule, a lipid or other biomolecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a target nucleic acid molecule. Alternatively, the specific binding partner may be coupled to a nucleic acid, which may act as a target nucleic acid molecule, or as a template for such a target nucleic acid molecule to be generated (e.g. an extension or ligation template).

Analytes of particular interest may thus include nucleic acid molecules, such as DNA (e.g. genomic DNA, mitochondrial DNA, plastid DNA, viral DNA, etc.) and RNA (e.g. mRNA, microRNA, rRNA, lncRNA, snRNA, viral RNA, etc.), and synthetic and/or modified nucleic acid molecules, (e.g. including nucleic acid domains comprising or consisting of synthetic or modified nucleotides such as LNA, PNA, base analogues, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g. through generation of a standard curve). Alternatively, relative quantification can be accomplished by comparison of detected levels or amounts between two or more different target analytes to provide a relative quantification of each of the two or more different analytes, i.e., relative to each other.

In one embodiment the method may be for the localised detection of target analyte. "Localised" detection means that the signal giving rise to the detection of the analyte is localised to the analyte, in this case the HCR product is localised to the target analyte. The analyte may therefore be detected in or at its location in the sample. In other words the spatial position (or localization) of the analyte within the sample may be determined (or "detected"). This means that the analyte may be localised to, or within, the cell in which it is expressed, or to a position within a cell or tissue sample. Thus "localised detection" may include determining, measuring, assessing or assaying the presence or amount and location, or absence, of the analyte in any way.

More particularly, the method may be used for the in situ detection of an analyte. In a particular embodiment, the method may be used for the localised, particularly in situ, detection of nucleic acids, particularly mRNA. More particularly, the method may be used for the localised, particularly in situ, detection of mRNA in a sample of cells. Alternatively, the method may be used for the in situ detection of a protein.

As used herein, the term "in situ" refers to the detection of a target analyte in its native context, i.e. in the cell or tissue in which it normally occurs. Thus, this may refer to the natural or native localization of a target analyte. In other words, the analyte may be detected where, or as, it occurs in its native environment or situation. Thus, the analyte is not moved from its normal location, i.e. it is not isolated or purified in any way, or transferred to another location or medium etc. Typically, this term refers to the analyte as it occurs within a cell or within a cell or tissue sample, e.g. its native localization within the cell or tissue and/or within its normal or native cellular environment. In particular, in situ detection includes detecting the target analyte within a tissue sample, and particularly a tissue section. In other embodiments the method can be carried out on a sample of isolated cells, such that the cells are themselves are not in situ.

In other embodiments, the detection is not localized, or not in situ. In other words, the method includes embodiments in which the target analyst is not present (e.g. is not fixed) in its native context. This may include embodiments in which a target analyte is immobilized, e.g. on a solid support. In still other embodiments, the method can be carried out in solution or in suspension. In particular the analyte can be in solution. Thus, for example, the method can be performed on a sample comprising an isolated analyte. In another embodiment the method can be performed where the analyte is suspended in a sample, for example where the analyte is a cell, or an aggregate etc. In still another embodiment, the analyte may be present in or on a cell which is in suspension in the sample, or which is immobilized in the sample etc.

The analyte is present within a sample. The sample may be any sample which contains any amount of target analyte which is to be detected, from any source or of any origin. A sample may thus be any clinical or non-clinical sample, and may be any biological, clinical or environmental sample in which the target analyte may occur. All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared for use in the method of the present invention, or they may be prior-treated in any convenient way e.g. for storage.

As noted above, in one embodiment, the target analyte may be detected in situ, as it naturally occurs in the sample. In such an embodiment the target analyte may be present in a sample at a fixed, detectable or visualisable position in the sample. The sample will thus be any sample which reflects the normal or native ("in situ") localisation of the target analyte, i.e. any sample in which it normally or natively occurs. Such a sample will advantageously be a cell or tissue sample. Particularly preferred are samples such as cultured or harvested or biopsied cell or tissue samples in which the target analyte may be detected to reveal the localisation of the target analyte relative to other features of the sample. In some embodiments, the sample may be a cell or tissue sample possessing a high autofluorescence, in particular a human tissue sample. In some embodiments, the sample may be a cancer tissue sample.

As well as cell or tissue preparations, such samples may also include, for example, dehydrated or fixed biological fluids, and nuclear material such as chromosome/chromatin preparations, e.g. on microscope slides. The samples may be freshly prepared or they may be prior-treated in any convenient way such as by fixation or freezing. Accordingly, fresh, frozen or fixed cells or tissues may be used, e.g. FFPE tissue (Formalin Fixed Paraffin Embedded). Analytes, including cells, or cells which carry or contain an analyte, may be immobilised on a solid support or surface, e.g. a slide, well or beads or other particles etc., using techniques and reagents well known the art, e.g. capture probes and such like, or by chemical bonding or cross-linking etc.

Thus, representative samples may include any material which may contain a target analyte, including for example foods and allied products, clinical and environmental samples, etc. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include clinical samples, e.g. whole blood and blood-derived products such as plasma, serum and buffy coat, blood cells, other circulating cells (e.g. circulating tumour cells), urine, faeces, cerebrospinal fluid or any other body fluids (e.g. respiratory secretions, saliva, milk, etc.), tissues, biopsies, as well as other samples such as cell cultures, cell suspensions, conditioned media or other samples of cell culture constituents, etc. The sample may be pre-treated in any convenient or desired way to prepare for use in the methods of the present invention, for example by cell lysis or purification, fixing of cells, isolation of the analyte, immobilisation etc.

Although the method of the present invention may be used to select a target analyte in an in situ (i.e. a native) setting, it is also contemplated that the method may be employed to select a target analyte in any detection system, including where a target analyte has been isolated or purified from its native setting. The sample may thus be a direct product of a target analyte isolation procedure, or of a cell lysis procedure, or it may further be fractionated or purified in some way. Thus, the analyte may be a synthetic molecule such as a cDNA or an amplicon etc., and the sample may be any material or medium containing such a molecule, e.g. a reaction mixture.

According to the method of the present invention, a target nucleic acid molecule is provided which is a target nucleic acid analyte (or a part thereof), or which has been generated from a target analyte or as a reporter for said analyte, and which comprises at least one copy of a marker sequence indicative of said analyte. The marker sequence is in turn involved in the initiation of the HCR reaction, the product of which is ultimately detected in order to indicate the presence of the target analyte. The marker sequence for a given target analyte must therefore be specific to that analyte, or unique, such that multiple target analytes can be distinguished from each other.

A "marker sequence" is thus a sequence which marks or identifies a given analyte. It is a sequence by which a given analyte may be detected and distinguished from other analytes. Where an "analyte" comprises a group of related molecules e.g. isoforms or variants or mutants etc., or molecules in a particular class or group, it is not required that a marker is unique or specific to only one particular analyte molecule, and it may be used to denote or identify the analyte as a group. However, where desired, a marker sequence may be unique or specific to a particular specific analyte molecule, e.g. a particular variant. In this way different variants, or isoforms, or mutants may be identified or distinguished from one another.

Where the target analyte is a nucleic acid molecule, the marker sequence may be a sequence present in the target analyte molecule, or a complement thereof (e.g. a reverse complement thereof). It may therefore be or comprise a variant or mutant sequence etc. present in the analyte, or a conserved sequence present in an analyte group which is specific to that group. The marker sequence may alternatively be incorporated into the target nucleic acid molecule as a tag or identifier (ID) sequence (e.g. a barcode) for the analyte (including for a nucleic acid analyte). It may thus be a synthetic or artificial sequence.

Where the target nucleic acid molecule is generated from a target analyte or as a reporter for said analyte, the marker sequence may be a complementary copy of a sequence present in a template which is used to generate the target nucleic acid molecule, for example, in a probe or a part thereof, e.g. where the target nucleic acid molecule is an amplification product, it may be a complementary to a sequence present in the template which is amplified. In an embodiment, the marker sequence may be a complementary copy of a sequence present in an RCA template, where the target nucleic acid molecule is an RCP. The RCA template may be part of a probe, or may be generated or provided in the assay method, for example by circularisation of a linear probe or probe component.

It can be seen that where the target nucleic acid molecule is generated directly from a target nucleic acid analyte then, again, the marker sequence may be the complement of a sequence present in the target analyte molecule. However, where the target nucleic acid molecule is generated from an alternative template (examples of which are set out below), the marker sequence may be the complement of a sequence present in said template. The marker complement sequence may thus be provided in the template for producing the target nucleic acid molecule as a tag or identifier sequence for the analyte, for example where the template for the target nucleic acid molecule is or is generated from a probe (e.g. a circularisable probe such as a padlock probe), or where the template for the target nucleic acid molecule is a reporter for the analyte (e.g. in an immunoRCA reaction). It will be understood in this regard that the sequence in the template which is complementary to the marker sequence present in the target nucleic acid molecule may itself be regarded as a marker sequence. The template may be provided or generated from a probe or reporter molecule which is designed to detect a particular analyte, and thus such a probe or reporter molecule may be viewed as comprising a marker sequence for that analyte—the marker sequence is then copied, as a complementary sequence, into the target nucleic acid molecule. The term "marker sequence" can therefore encompass both a marker sequence present in the target nucleic acid molecule and its complement (more particularly reverse complement) present in the template for the target nucleic acid molecule. Accordingly, a "marker sequence" can include the complementary sequence.

In some embodiments, the target nucleic acid molecule may be a hybridization probe comprising a target binding domain, which is capable of hybridizing to the target analyte, and an initiator binding domain, which comprises at least one copy of a marker sequence indicative of the target analyte. Accordingly, the hybridization probe may take the form of a so-called "L-probe". Such an L-probe may consist of two parts, a first part (the target binding domain) which binds to the target analyte, and a second part (the initiator binding domain) which does not hybridize to the target analyte and which consequently forms a single-stranded overhang when the probe is hybridized to the target analyte, which contains a binding site for an HCR initiator. In this form, the binding site for the HCR initiator would act as the marker sequence for the target analyte in question.

Similar two-part hybridization probes with alternative structures are known in the art. For example, a hybridization probe having a target binding domain and an initiator binding domain may have a hairpin structure comprising a double stranded stem region and a single stranded loop region. In some embodiments, the initiator binding domain may be comprised at least partially in the double stranded stem region. This arrangement prevents premature or unwanted initiation of the HCR reaction, as the initiator binding domain cannot hybridize to the HCR initiator and initiate an HCR reaction in the absence of the target nucleic acid molecule. Only when the target binding domain has hybridized to the target nucleic acid molecule, at which point the hairpin structure is disrupted and the hybridization probe unfolds, can the initiator binding domain hybridize to the HCR initiator and trigger the HCR reaction. Again, in this case, the binding site for the HCR initiator acts as a marker sequence.

Alternatively, the target nucleic acid molecule may be in the form of a ligatable probe provided in one or more parts. This ligatable probe may be a probe comprising multiple component parts which are capable of hybridizing to the target analyte such that they can be ligated together. The ligation reaction to join the components parts of the ligatable probe may result in the generation of a sequence which comprises a binding site for an HCR initiator. The probes may be arranged such that the binding site for the HCR initiator is only formed if all of the component parts of the ligatable probe are present and ligated together. In such embodiments, the marker sequence for the target analyte may be formed of sequences from one or more of the component parts of the ligatable probe. This arrangement prevents the HCR reaction from being inadvertently initiated in situations where the target analyte is not present, i.e. where not all of the component parts have hybridized to their respective targets, and may thus increase the signal to noise ratio that can be achieved by the method of the present invention. Alternatively, the target nucleic acid may be an amplicon or a complementary copy of such a probe which has been ligated. This approach is similar to that of the proximity assays discussed below, which also rely on a number of probe components being brought into proximity with each other via binding to their respective targets.

The ligatable probe may also be a probe which is capable of being circularised, such as a padlock probe or a molecular inversion probe, or the like. Such probes are well known and widely used and described in the art.

In some embodiments, the target nucleic acid molecule may be a rolling circle amplification product (RCP) generated from the target analyte or as a reporter for the target analyte. The RCP is generated by a rolling circle amplification (RCA) reaction using a circular RCA template molecule, that is a circular nucleic acid molecule. The RCA template may comprise the target analyte, or a part thereof, where the target analyte is a nucleic acid, or it may be provided or generated as a proxy, or a marker, for the analyte. The RCA template may thus be a probe, or a part or component of a probe, or may be generated from a probe, or it may be a component of a detection assay (i.e. a reagent in a detection assay), which is used as a reporter for the assay, or a part of a reporter, or signal-generation system. In short, the RCA template may be a circular (e.g. circularised) reporter nucleic acid molecule derived from any suitable RCA-based detection assay which uses or generates such a circular nucleic acid molecule as a reporter for the assay.

In some embodiments, where the target analyte is a nucleic acid molecule, the target analyte molecule itself which is present in the sample may be directly incorporated into the RCA template—in other words a target nucleic acid molecule, or a fragment thereof, may be circularised to form the RCA template. A marker sequence (specifically a marker complement sequence) present in the target analyte may thus be incorporated into the RCA template. Such a method may involve capture of a target nucleic acid fragment and circularisation, e.g. by ligation on a template. Probes are known in the art which may be used to capture and template the ligation of captured target nucleic acid molecules. Such circularisation adaptors include the so-called "Selector" probes of WO 2003/012119, WO 2005/111236, WO 2005/070630 and EP 1997909. Such probes have target binding regions designed to bind to the two respective ends of target nucleic acid fragments to bring them into juxtaposition for ligation together, directly or indirectly, to form a circular molecule of, or containing, the target nucleic acid fragment. A circularised Selector probe may contain the target nucleic acid analyte and a Selector probe sequence, for example where the Selector is a partially double-stranded construct comprising a long strand with single-stranded target-complementary end regions which hybridize to the respective ends of the target molecule and bring them into juxtaposition for ligation to the respective ends of the shorter strand of the Selector probe. As an alternative to using a marker sequence present in the analyte nucleic acid, a marker sequence may be contained in the shorter strand of the Selector probe which becomes ligated to the target molecule. Such probes are used to capture nucleic acid fragments and hence are not applicable to detection of nucleic acids in situ. Generally, a step of preparing fragments containing the target nucleic acid molecule is required.

Other types of probe may be used to generate circular molecules comprising a complementary copy of a target nucleic acid sequence, for example gap-filling padlock probes, or molecular inversion probes and such like. Alternatively, as described above, padlock probes may be used to detect target nucleic acids without generating a complementary copy of the target nucleic acid, wherein simply hybridization and ligation of the padlock probe on the target nucleic acid is detected, i.e. wherein the ligated padlock probe forms the target nucleic acid molecule, without an RCP being generated, although in another embodiment, a ligated padlock probe may be amplified, e.g. by RCA. All such probes may be used to detect nucleic acids in situ. The target nucleic acid, or a complementary copy thereof, may be used to prime the RCA of the circularised probe, and thereby localise the RCP to the target nucleic acid, thus enabling a localised detection.

As is clear from the above, the target analyte may be any nucleic acid molecule, including DNA, RNA, or a mixture thereof. Moreover, the target analyte may be any form of nucleic acid, such as mRNA, cDNA, etc. The sample may undergo any necessary treatments to prepare the target analyte for detection. In some embodiments, the RNA present in the sample may be reverse transcribed into cDNA, for example by contacting the sample with a reverse transcriptase enzyme and appropriate primers. Such enzymes and primers are well known in the art, and any suitable enzymes and primers may be employed. This reverse transcription reaction may be carried out in situ, following fixing of cells in the sample. In such an embodiment, the cDNA produced by the reverse transcription reaction can then be considered as the target analyte to be detected.

As is further clear from the above discussion, circularisable probes, or indeed more generally circularisable reporter molecules, may be used to generate an RCA template which is used to generate an RCP as the target nucleic acid molecule. By "circularisable" is meant that the probe or reporter (the RCA template) is in the form of a linear molecule having ligatable ends which may circularised by ligating the ends together directly or indirectly, i.e. to each other, or to the respective ends of an intervening ("gap") oligonucleotide or to an extended 3' end of the circularisable RCA template. A circularisable template may also be provided in two or more parts, namely two or more molecules (i.e. oligonucleotides) which may be ligated together to form a circle. When said RCA template is circularisable it is circularised by ligation prior to RCA. Ligation may be templated using a ligation template, and in the case of padlock and molecular inversion probes and such like the target analyte may provide the ligation template, or it may be separately provided. The circularisable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In the case of padlock probes, in one embodiment the ends of the padlock probe may be brought into proximity to each other by hybridization to adjacent sequences on a nucleic acid molecule which is the target for the padlock probe (such as a target analyte), and which acts as a ligation template. This allows the ends of the padlock probe to be ligated together to form a circular nucleic acid molecule, allowing the circularised padlock probe to act as a template for an RCA reaction. In such an example, the terminal sequences of the padlock probe which hybridize to a nucleic acid target analyte will be specific to the target analyte in question, and will be replicated repeatedly in the RCP. They may therefore act as a marker sequence indicative of that target analyte. Accordingly, it can be seen that the marker sequence in the RCP may be equivalent to a sequence present in the target analyte itself. Alternatively, a marker sequence (e.g. tag or barcode sequence) may be provided in the non-target complementary parts of the padlock probe. In still a further embodiment, the marker sequence may be present in the gap oligonucleotide which is hybridized between the respective hybridized ends of the padlock probe, where they are hybridized to non-adjacent sequences in the target analyte molecule. Such gap-filling padlock probes are akin to molecular inversion probes.

Accordingly, similar circular RCA template molecules can be generated using molecular inversion probes. Like padlock probes, these are also typically linear nucleic acid molecules capable of hybridizing to a target nucleic acid molecule (such as a target analyte) and being circularised. The two ends of the molecular inversion probe may hybridize to the target nucleic acid molecule at sites which are proximate but not directly adjacent to each other, resulting in a gap between the two ends. The size of this gap may range from only a single nucleotide in some embodiments, to larger gaps of 100 to 500 nucleotides, or longer, in other embodiments. Accordingly, it is necessary to supply a polymerase and a source of nucleotides, or an additional gap-filling oligonucleotide, in order to fill the gap between the two ends of the molecular inversion probe, such that it can be circularised.

As with the padlock probe, the terminal sequences of the molecular inversion probe which hybridize to the nucleic acid target analyte, and the sequence between them, will be specific to the target analyte in question, and will be replicated repeatedly in the RCP. They may therefore act as a marker sequence indicative of that target analyte. Alternatively, a marker sequence (e.g. tag or barcode sequence) may be provided in the non-target complementary parts of the molecular inversion probe.

Other types of probe which result in circular molecules comprising either a target analyte sequence or a complement thereof, which can act either as target nucleic acid molecules themselves, or templates for producing RCPs to act as target nucleic acid molecules, have been developed by Olink Bioscience (now Navinci Diagnostics AB). These include the Selector-type probes described in WO 2016/016450, which comprise sequences capable of directing the cleavage of a target nucleic acid molecule (i.e. a target analyte) so as to release a fragment comprising a target sequence from the target analyte and sequences capable of templating the circularisation and ligation of the fragment. WO 2016/016452 describes probes which comprise a 3' sequence capable of hybridizing to a target nucleic acid molecule (i.e. a target analyte) and acting as a primer for the production of a complement of a target sequence within the target nucleic acid molecule (i.e. by target templated extension of the primer), and an internal sequence capable of templating the circularisation and ligation of the extended probe comprising the reverse complement of the target sequence within the target analyte and a portion of the probe. In the case of both such probes, target sequences or complements thereof are incorporated into a circularised molecule which acts as the template for the RCA reaction to generate the RCP, which consequently comprises concatenated repeats of said target sequence. Again, said target sequence may act as, or may comprise a marker sequence within the RCP indicative of the target analyte in question. Alternatively, a marker sequence (e.g. tag or barcode sequence) may be provided in the non-target complementary parts of the probes.

As noted above, in some embodiments the present method may use as a target nucleic acid molecule an RCP which has been generated as a reporter for the target analyte. In such embodiments, an RCA reaction may be performed to amplify a circular nucleic acid molecule (RCA template)

which is a reporter for the presence of the target analyte. Such an RCA template may contain a marker sequence (or more particularly a complement thereof), in order to produce an RCP comprising multiple repeat copies of a marker sequence indicative of said target analyte. In this case, the method may be used for the detection of any target analyte, including a nucleic acid molecule, or an analyte other than a nucleic acid molecule, such as a protein, peptide, lipid etc. In such embodiments, the marker sequence is a sequence other than a sequence that is present in the target analyte itself. The marker sequence may be present in a probe molecule (such as padlock or molecular inversion probe, or any other probe described or mentioned above), or it may be present in a circular or circularisable nucleic acid reporter molecule which is used in conjunction with a probe to detect the target analyte.

A variety of assays have been developed wherein a nucleic acid molecule (e.g. probe or reporter molecule) may be used to directly or indirectly "tag" or "label" a target analyte in a sample. In such embodiments, this may be a circular or circularisable nucleic acid molecule, which may provide a template for an RCA reaction, thereby effecting the generation of an RCP as target nucleic acid molecule capable of acting as a reporter for the target analyte. The marker sequence present in such a target nucleic acid molecule, which is indicative of said target analyte, may thus be a complementary copy of a sequence present in the probe. This marker sequence will be associated with the target analyte via the probe or reporter, when the probe is bound to the analyte, and if necessary when the probe or reporter is circularised, such that detection of the target nucleic acid molecule, indirectly via detection of the product of the subsequent HCR reaction, serves to indicate the presence of the target analyte in the sample.

In some methods, a new nucleic acid molecule may be generated in a sample, i.e. a nucleic acid molecule that was not present in the original sample and was not one of the components added to the sample). This may be generated by one or more molecules that interact with, e.g. bind to, the target analyte. The generated nucleic acid molecule may thus act as the target nucleic acid molecule, in that the detection of the generated nucleic acid molecule is indicative of the target analyte in a sample. The generated molecule may be a circular molecule, or it may template the circularisation of another molecule, such as a padlock probe for the generated molecule.

Various methods based upon detecting such a proxy or marker nucleic acid molecule using an RCA reaction as part of the detection strategy, i.e. for generating a target nucleic acid molecule indicative of the target analyte, are well described in the art, including, for example, immunoRCA, assays using padlock probes and proximity probe assays which generate a circular nucleic acid molecule. In all these cases, the methods rely on providing or generating a circular nucleic acid molecule which may then be used as a substrate (template) for an RCA reaction, and the resulting RCA product may then act as a target nucleic acid molecule capable of being a reporter for the analyte, i.e. as a substitute for detecting the target analyte directly.

ImmunoRCA typically uses a conjugate comprising an antibody specific for a target analyte linked to an oligonucleotide, although any binding partner specific for the analyte may be used. The target analyte is contacted with the antibody:oligonucleotide conjugate. A circular or circularisable oligonucleotide (such as a padlock probe or similar, for example), is hybridized to the oligonucleotide conjugated to the antibody (the circular/circularisable oligonucleotide may be pre-hybridized or added after the antibody has been allowed to interact with the target analyte). The sample is then subjected to an RCA reaction to amplify the circular/circularised oligonucleotide. The circular or circularisable oligonucleotide provided as the RCA template in an immunoRCA method may comprise a marker sequence. In this way, the resulting target nucleic acid molecule (RCP) comprises multiple repeat copies of the marker sequence.

This method also has the advantage that the oligonucleotide conjugated to the antibody is used as the primer for the RCA reaction. As a result of this arrangement, the target nucleic acid molecule produced is tethered to the antibody that is interacting with the target analyte, thereby allowing localised detection of the analyte in the sample. This is particularly useful in in situ applications, e.g. in a cell or tissue sample, where information about the location of different target analytes within the cell or tissue can be obtained.

Proximity assays may also be designed for use with an RCA-based detection system, wherein a circular nucleic acid molecule is generated as a result of the interaction of the interaction of the nucleic acid domains of proximity probes with each other, or with added oligonucleotides. As outlined above, in a proximity assay, a target analyte is detected by the binding of multiple (i.e. two or more, generally two or three) probes which, when brought into proximity to each other by binding to the target analyte (hence "proximity probes"), allow a signal to be generated. Typically, the proximity probes each comprise a nucleic acid domain linked to the target-analyte-binding domain of the probe, and generation of the signal involves an interaction between the nucleic acid moieties. Thus, signal generation is dependent on an interaction between the nucleic acid moieties and hence only occurs when the probes have both (or all) bound to the target analyte, thereby lending improved specificity to the detection system.

For example, proximity ligation assays (PLAs) rely on proximal binding of proximity probes to an analyte to generate a signal from a ligation reaction involving or mediated by (e.g. between and/or templated by) the nucleic acid domains of the proximity probes. Such a ligation reaction may result in the generation of a circular nucleic acid molecule, or indeed, in an alternative embodiment, a linear nucleic acid molecule. Such a ligation product, or an amplification product thereof, may represent the target nucleic acid molecule. Proximity extension assays (PEAs) may generate an extended nucleic acid molecule wherein the nucleic acid domain of one proximity probe is extended using the nucleic acid domain of another proximity probe as extension template. The extended molecule, or an extended part thereof, may represent the target nucleic acid molecule. Alternatively, the extended molecule may be detected by hybridization of a circular or circularisable oligonucleotide which acts as a RCA template for a RCA reaction to generate an RCP as the target nucleic acid molecule.

The nucleic acid domains of the proximity probes when in proximity may template the ligation of one or more added oligonucleotides to each other, including an intramolecular ligation, to circularise one or more added linear oligonucleotides, to form a nucleic acid circle, based on the padlock probe principle, as described, for example, by Landegren et al. in WO 99/49079. In such a method, the ends of the added linear oligonucleotide(s) are brought into juxtaposition for ligation by hybridizing to one or more circularisation templates provided by the nucleic acid domain of one or more proximity probes. Various such assay formats are described in WO 01/61037.

It will be understood that the target nucleic acid molecule that is provided in the method of the present invention may be used to detect any target analyte in a sample, regardless of whether it has been generated from the target analyte, i.e. from the "original" nucleic acid molecule in a sample, where the target analyte is a nucleic acid; or whether it is generated as a reporter for the target analyte, and is derived from a "proxy" nucleic acid molecule provided in a detection assay, or generated, for example by the interaction of specific detection molecules, e.g. immunoRCA or proximity probes, with the target analyte, e.g. where the target analyte is a protein.

Alternatively put, the target nucleic acid molecule that is provided in the method of the present invention may be any suitable nucleic acid molecule which can be generated in the course of a detection assay. Since the target nucleic acid molecule may be generated according to known assay methods, the performance of steps of the method leading to the generation or provision of the target nucleic acid molecule will thus generally be according to methods and principles well known and understood in the art.

In certain preferred embodiments, the target nucleic acid molecule provided in the present method is an RCP, or other amplification product. Accordingly, in order to generate an RCP or other amplification product to act as a reporter for a target analyte, a sample containing the analyte may be incubated with probes, to allow the probes to bind or interact with the analyte, e.g. to hybridize to a nucleic acid analyte, or for antibody-based probes to bind to the analyte. As discussed above, probes can be designed or selected which comprise, or which generate, or which lead to the generation of, an amplification template, e.g. a RCA template. Alternatively, the target nucleic acid molecule may itself be a probe or probe component, or a circularised probe etc., and the method here will also comprise a probe incubation step. Conditions for such an incubation step are known in the art, and may be varied according to the sample, or analyte, or probes used, etc. This may include washing steps to remove unbound probes etc. Where necessary, this may be followed by a reaction to circularise a circularisable probe or reporter molecule, again according to well-known procedures. Ligation reactions for circularisation of such probes or reporter molecules are also well known and described in the art, and a variety of different template-directed ligases may be used, including temperature sensitive and thermostable ligases, such as bacteriophage T4 DNA ligase, bacteriophage T7 ligase, *E. coli* ligase, Taq ligase, Tth ligase, Ampligase® and Pfu ligase. Certain RNA ligases may also be employed in the methods of the invention. A suitable ligase and any reagents that are necessary and/or desirable may be combined with the sample/reaction mixture and maintained under conditions sufficient for ligation to occur. Ligation reaction conditions are well known in the art and may depend on the ligase enzyme used.

The next step following a ligation step (if required) is to generate the amplification product, e.g. an RCP. Amplification techniques, including e.g. PCR and RCA, are well known in the art, and procedures are widely described in the literature. The primer for the amplification (e.g. RCA) will depend on the assay format, and may be provided by a target nucleic acid analyte (e.g. to which a circularisable probe has hybridized), by a probe or a part thereof, e.g. by the conjugated oligonucleotide of an immunoRCA probe or the nucleic acid domain of a proximity probe, or it may be separately provided. A RCA primer or other amplification primer will be of sufficient length, to provide for hybridization to the template (e.g. RCA template) under annealing conditions.

In addition to the above components, the reaction mixture for amplification mixture will contain other reagents necessary for an amplification reaction, for example a polymerase enzyme and nucleotides. In the case of RCA, the RCA reaction mixture includes a polymerase, e.g. phi29 polymerase, and other components required for a DNA polymerase reaction. The desired polymerase activity may be provided by one or more distinct polymerase enzymes. In some embodiments the polymerase has exonuclease activity, e.g. 5' and/or 3' exonuclease activity. 3' exonuclease activity may be desirable, in order to digest the 3' end of a probe or target molecule to generate a hybridized 3' end (to the RCA template) which can act as a primer for the RCA reaction.

In preparing the reaction mixture of this step of the method, the various constituent components may be combined in any convenient order. For example, all of the various constituent components may be combined at the same time to produce the reaction mixture.

Regardless of the type of target nucleic acid molecule that is provided in the present method, and the mechanism by which it is generated, the target nucleic acid molecule comprises at least one copy of a marker sequence which is indicative of the target analyte. The marker sequence is used in the initiation of the HCR reaction, either directly as a HCR initiator (i.e. the marker sequence is or comprises a sequence which functions as a HCR initiator) or as binding site for a separately-provided HCR initiator. The HCR initiator triggers an HCR reaction, the polymeric product of which is ultimately detected in order to indicate the presence of the target analyte.

In some embodiments, for example, the present method may provide a single target nucleic acid molecule for each target analyte. Such a target nucleic acid molecule may comprise a single copy of a marker sequence, allowing a single HCR initiator to be bound. If this HCR initiator is capable of triggering a single HCR reaction, then it can be seen that the provision of a single target molecule per target analyte results in the production of a single HCR product. Alternatively put, there is a 1:1 ratio between HCR products and target analytes.

However, in some embodiments, the step (ii) of performing an HCR reaction involves generating multiple HCR products for each target analyte. In such an embodiment, multiple HCR products may be generated in a single (or individual) HCR reaction, in the sense of a single (or individual) performance of the HCR reaction, i.e. in a single or individual HCR run or "cycle". Alternatively, multiple HCR products may be generated at one time, or simultaneously (as will be described below, in some embodiments sequential HCR steps may be performed, i.e. two or more cycles of HCR, for example in combinatorial labelling schemes). In such embodiments, where multiple HCR products are generated in an individual HCR reaction, the ratio between HCR products and target analytes will be greater than 1:1, i.e. there will be more HCR products than target analytes. The factor by which this signal is amplified, i.e. the number of HCR products which are generated from each target analyte, may be referred to as the amplification factor. An amplification factor of 3, for example, would mean that 3 HCR products are produced for each target analyte, i.e. the ratio of HCR products to target analytes is 3:1. In some embodiments, the ratio of HCR products to target analytes may be at least 3:1, e.g. at least 4:1, 5:1, 6:1, 7:1, 8:1, 9:1, or more. Preferably the ratio of HCR products to target analytes may be at least 10:1, more preferably the ratio may be at least 50:1, at least 100:1, at least 250:1, at least 500:1, at least 1000:1, at least 5000:1 or at least 10000:1. Alternatively put, the present method may involve an amplification factor of at least 3, e.g. at least 4, 5, 6, 7, 8, 9, or more. Preferably the amplification factor may be at least 10, more preferably at least 50, at least 100, at least 250, at least 500, at least 1000, at least 5000 or at least 10000. The amplification ratio/factor will depend on the nature of the target nucleic acid molecule. For example if it is an amplification product such as an RCP which contains many multiple copies of the RCA template, then this can provide a very high number of potential HCR initiators or binding sites for an HCR initiator, e.g. hundreds or thousands. This may also depend on the nature of the sample, and whether, for example a RCP is generated in solution or in situ in a tissue sample. The amplification factor is not critical and can be varied in a large range depending on the circumstances.

There are a number of stages in the present method at which the amplification factor can be increased in order to generate multiple HCR products for each target analyte. This may comprise the use of multiple components or reagents for the method. The term "multiple" as used herein, or "multiplicity" or such like, means two or more, e.g. at least 2, 3, 4, 5, 6, 10, 20, 30, 50, 70 or 100, 200, 500, 1000 or more.

Firstly, multiple target nucleic acid molecules may be provided for each target analyte. In some embodiments, for example, multiple target nucleic acid molecules may be provided in the form of multiple probes, e.g. hybridization probes, or antibody-based or other probes comprising a nucleic acid molecule, for each target analyte. Each of the multiple probes may represent, or may comprise, or lead to the generation of, a target nucleic acid molecule. By way of representative example, multiple padlock probes, each comprising the same marker sequence, may hybridize to a single nucleic acid target analyte. Thus, for example, if 3 target nucleic acid molecules are provided or generated as reporters for each target analyte, with each target nucleic acid molecule comprising a single copy of a marker sequence, then 3 HCR initiators can be bound for each target analyte (one at each target nucleic acid molecule); 3 HCR reactions can be initiated (one by each initiator) and 3 HCR products can be generated (one from each reaction), from a single target analyte. The target nucleic acid molecule may in such a case be a single probe molecule, or a single probe component, and multiplicity may be achieved by providing multiple probes etc.

Similarly, each target nucleic acid molecule may comprise multiple copies of the marker sequence. Thus a probe molecule, or probe component, including a padlock probe as described above, may comprise multiple copies of a marker sequence. In another example, an amplification product may be generated which comprises multiple copies of the marker sequence. In an embodiment, where the target nucleic acid molecule is an RCP, i.e. a concatemer of monomer repeats produced by repeated amplification of a circular template, the target nucleic acid molecule will comprise a plurality of marker sequences. Accordingly, when the target nucleic acid molecule comprises multiple copies of the marker sequence, multiple HCR initiators will be comprised within, or can be hybridized to, each target nucleic acid molecule. In turn, this means that multiple HCR reaction can be initiated, and multiple HCR products can be generated, from a single target analyte.

Finally, each marker sequence may bind an HCR initiator capable of initiating multiple HCR reactions. As will be discussed in more detail below, the HCR initiator may be in the form of an HCR initiator complex, which is capable of supporting multiple HCR reactions, such that multiple HCR reactions can be initiated from each marker sequence. Accordingly, even from a single target nucleic acid analyte comprising a single copy of a marker sequence, multiple HCR products can be generated.

It will be understood that these methods of increasing the signal amplification factor may readily be employed together, in any suitable combination, so as to maximise the number of HCR products generated from each target analyte. For example, it would be possible to employ a system wherein each target analyte is tagged or labelled by multiple target nucleic acid molecules; each target nucleic acid molecule comprising multiple copies of a marker sequence; and each marker sequence hybridizing an HCR initiator complex capable of supporting multiple HCR reactions. Such a system would involve 3 separate stages of signal amplification, and would thus be capable of achieving a significant amplification factor. As noted above, any other appropriate combination of the signal amplification methods disclosed herein is also contemplated.

By way of example, in an embodiment, an RCP may be generated comprising multiple repeat copies of a sequence which is targeted by a probe. Multiple probes may thus be bound. Each probe may comprise multiple marker sequences, each of which comprises, or is capable of hybridizing to, a HCR initiator.

It will be understood that generating multiple HCR products for each target analyte results in an amplification of the signal associated with each target analyte, relative to a method as described above, where the provision of a single target analyte results in the production of a single HCR product. An increase in the number of HCR products per target analyte therefore results in a strong signal intensity, and thus an increase in the signal to noise ratio which can be achieved using the present method. In turn, this allows for highly sensitive detection of target analytes, and enables, for example, the detection of rare transcripts or mutations. The methods described above which involve significant amplification factors are thus of particular use in detecting target analytes in samples which feature a high level of autofluorescence, such as the majority of human tissue samples.

In order to achieve the aforementioned levels of signal amplification, it may be advantageous to provide in step (i) of the present method, as a target nucleic acid molecule, a so-called nucleic acid accumulation (NAA). An NAA comprises one or more nucleic acids comprising a target sequence which is present in high concentration or high copy number at a spatially defined site. In the case of the present method, the target sequence in the NAA may be a marker sequence. Alternatively, a NAA may be provided to provide a binding site for multiple target nucleic acid molecules.

NAAs may originate from localized DNA amplification mechanisms. Any such DNA amplification method may be used to generate NAAs, including polymerase chain reaction (PCA), helicase-dependent amplification (HDA), loop mediated isothermal amplification (LAMP), multiple strand displacement amplification (MDA) or rolling circle amplification (RCA). An RCP is thus a typical NAA. It will be understood that such a DNA amplification reaction may be carried out on any appropriate substrate. For example, NAAs may be generated by using a proximity ligation assay (PLA), wherein the PLA reporter molecule is subjected to an RCA reaction, or by using immunoRCA, as described above.

The use of an RCP as a target nucleic acid molecule in the present method is particularly advantageous because of the high copy number of the marker sequence in the concatenated product. This results in a high local concentration of marker sequences in the locality of the target analyte, and multiple HCR initiators contained within, or hybridized on, the target nucleic acid molecule (the RCP), as the RCP contains multiple HCR initiators or binding sites for HCR initiators.

Other NAAs may also be used, however. For example, NAAs may be generated by using hybridization probes as target nucleic acid molecules, wherein several hybridization probes are bound to proximal locations on the same target analyte (or probe, or part thereof, for the target analyte). Where the hybridization probes bind to a probe, or part thereof, for the target analyte, the probe may serve as a guiding template or scaffold for the spatial accumulation of these hybridization probes into a distinct spatial position defined by the location of the target analyte. This similarly results in a high local concentration of marker sequences in the locality of the target analyte, due to the high local concentration of target nucleic acid molecules.

Where a separate HCR initiator is used, as opposed to an HCR initiator comprised within the marker sequence of the target nucleic acid molecule, the present method may thus comprise hybridizing a multiplicity of HCR initiators to the target nucleic acid molecule(s), or more particularly to the marker sequences present in the target nucleic acid molecule(s), for example to either monomer repeats in an RCP, multiple proximate hybridization probes, or any other suitable arrangement of marker sequences in one or more target nucleic acid molecules.

It will be understood that in the case of a target nucleic acid molecule comprising multiple marker sequences, whilst each of the marker sequences comprises a binding site for an HCR initiator, in practice not all of these binding sites may (or will) be occupied by an initiator after initiator hybridization. It suffices that a number, or multiplicity, of such binding sites are bound by an initiator. Thus, in the method the initiator may hybridize to at least one marker sequence present in a target nucleic acid molecule (e.g. to a marker sequence in at least one monomer of an RCP), but preferably to multiple marker sequences.

In certain embodiments, the method relies upon multiple HCR initiators or HCR monomers being able to hybridize to the target nucleic acid molecule(s). Accordingly, it will be understood that in such embodiments the target nucleic acid molecule(s) needs to be available for such hybridization. Thus, it may be advantageous for the target nucleic acid molecule(s) to have low secondary structure. However, this feature may be compensated for by performing the method in conditions which favour hybridization, according to principles well known in the art. Thus, for example, the method can be performed in the presence of formamide e.g. in buffers containing formamide.

As noted above, the method of the present invention uses HCR monomers having a single-stranded linear structure. Unlike conventional HCR monomers, these HCR monomers do not contain any hairpin or stem-loop structures, or any bulge-loop or mismatched hairpin structures. More particularly, these HCR monomers do not contain any secondary structure at all, but are single-stranded and linear. Accordingly, the method of the present invention uses HCR monomers which may lack any significant regions of self-complementarity, i.e. regions of self-complementary which would be sufficiently large to hybridize to one another and to induce the formation of a region of secondary structure in the HCR monomer.

In the simplest form of HCR, two different types of HCR monomer, referred to here as first and second HCR monomers, undergo a chain reaction of hybridization events to form a long nicked double-stranded DNA molecule when an "initiator" nucleic acid molecule is introduced. The HCR monomers each comprise an "input domain" and an "output domain". The HCR initiator may also comprise an "output domain", which is capable of triggering the HCR polymerisation reaction, i.e. of initiating the HCR reaction. In the case of the HCR initiator the output domain may be referred to as the "initiator domain". The first HCR monomers have an input domain complementary to the output domain (initiator domain) of an HCR initiator and the output domain of the second HCR monomers; and an output domain complementary to the input domain of the second HCR monomers. Similarly, the second HCR monomers have an input domain complementary to the output domain of the first HCR monomers; and an output domain complementary to the input domain of the first HCR monomers. At their simplest, the nucleic acid sequence of a HCR monomer may consist of two parts, an input domain and an output domain. Thus a HCR monomer may consist of an input domain, an output domain, and optionally a label. However, as described further below, the HCR monomer may also comprise other parts or domains, for example, a binding domain for a displacer probe (see below), or a recognition or detection domain, for example to bind a detection probe, etc.

Accordingly, once the HCR initiator and the HCR monomers are introduced, the initiator domain of the initiator can hybridize to the input domain of a first HCR monomer; the output domain of said first HCR monomer can hybridize to the input domain of a second HCR monomer; the output domain of said second HCR monomer can hybridize to the input domain of another first HCR monomer; and so the reaction can continue in this manner, incorporating HCR monomers into a growing polymeric chain until all of the monomers are exhausted. Ultimately, this chain reaction leads to the formation of a nicked chain of alternating units of the first and second monomer species. The presence of the HCR initiator is thus required in order to trigger the HCR reaction at the target nucleic acid molecule by hybridization to a first HCR monomer. It will be understood that first and second HCR monomers, although they are devoid of secondary structure and do not need to be "triggered" (or opened) in order to hybridize to one another, will not bind, and hence will not be triggered to be localised, at the target nucleic acid molecule, and hence at the analyte, in the absence of the HCR initiator, or the target nucleic acid molecule. As noted above, first and second HCR monomers (or indeed any further HCR monomers) designed to hybridize to one another are defined as cognate to one another. They are also cognate to a given HCR initiator sequence. HCR monomers which interact with one another (hybridize) may be described as a set of HCR monomers or a HCR monomer, or hairpin, system.

It can be seen that the HCR reaction could be carried out with more than two species or types of HCR monomers. For example, a system involving three HCR monomers could be used. In such a system, each first HCR monomer may comprise an output domain which is complementary to the input domain of a second HCR monomer; each second HCR monomer may comprise an output region which is complementary to the input domain of a third HCR monomer; and each third HCR monomer may comprise an output domain which is complementary to the input domain of a first HCR monomer. The HCR polymerisation reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described, and these may be used in the methods herein.

The HCR initiator used in the method of the present invention is provided in one or more parts, and either hybridizes to the marker sequence in the target nucleic acid molecule, or is comprised within said marker sequence. Where the HCR initiator is a sequence comprised within the marker sequence of the target nucleic acid molecule, the input domain of the first HCR monomer may hybridize to it. In other words, the marker sequence comprises a sequence complementary to at least part of the input domain of a first HCR monomer. Such a complementary sequence may be viewed as the initiator domain of the HCR initiator.

In the case where the HCR initiator is a separate molecule comprising a sequence capable of hybridizing to the marker sequence, the HCR initiator may comprise a region of complementarity to the marker sequence, that is a marker-binding sequence, i.e. a target nucleic acid molecule binding region or domain (or more particularly a marker sequence binding-domain), and a second domain, which does not bind to the target nucleic acid molecule and which contains a sequence complementary to a sequence within the input domain of a first HCR monomer. Such a sequence is the sequence which initiates the HCR reaction, and may be viewed as the "initiator sequence" (or initiator domain).

The length of an HCR monomer or the domains thereof is not critical and may be varied according to choice and design of the HCR monomer sets etc. This is within the routine skill of the person skilled in the art. In some embodiments, an LO-HCR monomer is between about 10 and about 100 nucleotides in length. For example, the total length of an LO-HCR monomer may be 16 to 60 nucleotides in length, e.g. 20 to 60, 20-50, 20 to 40, 20-30, 22-30, 24-30, or 26-30 nucleotides in length, for example, 26, 28 or 30 nucleotides. The length of a input or output domain may be, by way of example, 8 to 30 nucleotides in length, e.g. 10 to 30, 10-25, 10 to 20, 10-15, 11-15, 12-15, or 13-15 nucleotides in length, for example, 13, 14 or 15 nucleotides.

The method of the present invention uses an HCR initiator which is provided in one or more parts. In some embodiments, the HCR initiator may be provided in a single part, i.e. as a single molecule. Alternatively, the HCR initiator may be provided in two or more parts.

The initiator may in some embodiments initially be "protected" or shielded from being able to hybridize to the first HCR monomer and thereby initiate an HCR reaction before hybridization to the target nucleic acid molecule. This protection or shielding of the HCR initiator may be provided in the form of a metastable secondary structure (more particularly a double stranded metastable secondary structure, e.g. a stem-loop structure). Interaction of the initiator with the marker sequence of the target nucleic acid molecule, for example, can cause the metastable secondary structure to be disrupted, or unfolded (namely "opened up"), thereby exposing the HCR initiator which is then free to hybridize to the first HCR monomer and trigger the HCR reaction at the target nucleic acid molecule.

Various HCR initiator designs have been proposed, which may include metastable hairpin structures as described above, and/or which comprise "bridge" molecules, wherein the actual initiator sequence is hybridized to a pair of bridge molecules which each hybridize to the target nucleic acid molecule (e.g. the RCP), or wherein the initiator is "split" and provided in two parts, which each hybridize to their target molecule (e.g. the RCP), in order to together provide a complete HCR initiator. See for example the designs HCR v2.0 and HCR v3.0 described by Choi et al., 2018, Development 145(12) dev165753. Any such initiator designs may be used in the method.

Accordingly, it will be understood that the HCR initiator may comprise multiple component parts, e.g. multiple oligonucleotide components. The HCR initiator may thus be in the form of an initiator complex.

In some embodiments, the HCR initiator complex may comprise; (i) an oligonucleotide having a marker sequence binding-domain and an initiator domain; and (ii) a first HCR monomer, hybridized to the initiator domain of the oligonucleotide of (i). Such an HCR initiator complex may be referred to as a "primed" initiator complex, as it is primed with the first HCR monomer. Alternatively put, the first HCR monomer may be pre-bound, such that it forms part of the HCR initiator complex which initiates the HCR reaction. When such a primed HCR initiator complex is used in the present method, the next step in the HCR reaction would be the hybridization of a second HCR monomer to the output domain of the first HCR monomer of the initiator complex. It will be understood that a single copy of such a primed HCR initiator complex is capable of initiating a single HCR reaction, and thus of generating a single HCR product.

Alternatively, the HCR initiator complex may be capable of supporting multiple HCR reactions, such that multiple HCR reactions can be initiated from each marker sequence. As noted above, such an initiator complex can boost the signal that is obtained from each target analyte, and thus can increase the signal to noise ratio of the present method, allowing for increased sensitivity in the detection method.

The HCR initiator complex may take any suitable form which allows for multiple HCR reactions to be initiated from a single marker sequence. Such an HCR initiator complex can be considered as having a first initiator component, which hybridizes to the marker sequence in the target nucleic acid molecule, and two or more additional initiator components, which are involved in initiating HCR reactions. In other words, the initiator complex may, in an embodiment, comprise a single first marker-binding component and multiple additional components each comprising an initiator domain. The additional components may each be capable of binding to the first component and/or to another additional component. Accordingly, the HCR initiator complex may comprise a first initiator component having a marker sequence binding-domain and two or more output domains, which are each capable of hybridizing to additional components of the HCR initiator complex. The HCR initiator complex will further comprise two or more additional initiator components, each comprising an input domain, which contains a sequence complementary to an output domain of the first initiator component, and an initiator domain, which contains a sequence complementary to a sequence within the input domain of a first HCR monomer.

In some embodiments, the number of additional initiator components will be equal to the number of output domains in the first initiator component. For example, if the first initiator component comprises a marker sequence-binding domain and two output domains, the HCR initiator complex would further comprise two additional initiator components, each comprising an input domain which contains a sequence complementary to an output domain of the first initiator component, and an initiator domain, which contains a sequence complementary to a sequence within the input domain of a first HCR monomer.

In a further embodiment, the additional initiator components may comprise, in addition to the aforementioned input domain and initiator domain, an output domain capable of hybridizing to further additional components of the HCR initiator complex. This arrangement would allow each additional initiator component of the HCR initiator complex to support multiple HCR reactions—one HCR reaction would be initiated through the initiator domain, and further HCR reactions would be initiated by the further additional initiator components which hybridize to the output domain.

In some embodiments, the input domain of an additional initiator component may hybridize to the output domains of multiple other initiator components. The additional initiator component may, for example, hybridize via an input domain to an output domain of the first initiator component, and an adjacent output domain of an additional initiator component. Alternatively, the additional initiator component may hybridize via an input domain to adjacent output domains of two additional initiator components. The HCR initiator complex may thus comprise a Holliday junction, formed of multiple initiator components comprising input and output domains which are complementary to each other.

Figure 10:
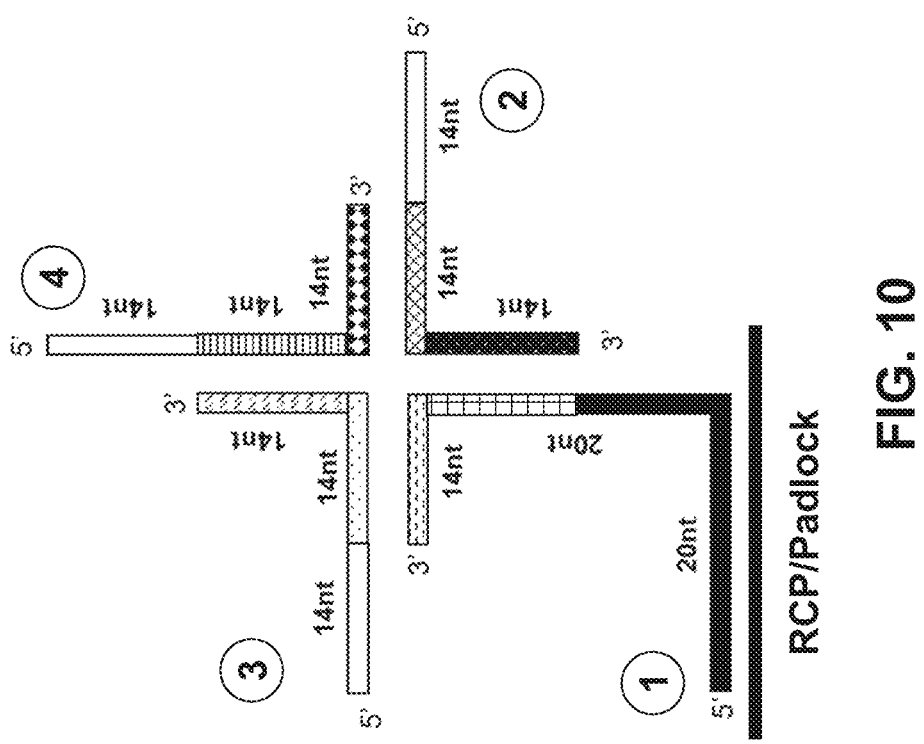
FIG. 10 shows a schematic of an exemplary LO-HCR initiator complex comprising first, second, third and fourth initiator components.

In a specific embodiment, the HCR initiator complex may be capable of supporting 3 HCR reactions, such that 3 HCR reactions can be initiated from each marker sequence. Methods involving the use of this particular design of initiator complex are termed "LO-HCRplus" herein. The initiator complex used in the LO-HCRplus method comprises four HCR initiator components, and is shown in FIG. 10. The first initiator component comprises a marker sequence-binding domain, and two output domains. The second and third initiator components (additional initiator components) each comprise an input domain, which contains a sequence which is complementary to an output domain of the first initiator component; an initiator domain, which contains a sequence complementary to a sequence within the input domain of a first HCR monomer; and an output domain, which contains a sequence which is complementary to a portion of the fourth initiator component. The fourth and final initiator component in this design comprises an input domain which contains a sequence which is complementary to the output domain of the second initiator component and a sequence which is complementary to the output domain of the third initiator component; and an initiator domain, which contains a sequence complementary to a sequence within the input domain of a first HCR monomer. Accordingly, an immobile Holliday junction is formed between the four components of the HCR initiator complex. Each of the three additional initiator components is capable of initiating an HCR reaction, and thus the LO-HCRplus initiator complex as a whole is capable of supporting 3 HCR reactions.

The HCR initiator complexes discussed above which are capable of supporting multiple HCR reactions may be assembled prior to contacting the target nucleic acid molecule with the initiator complex. In such embodiments, the components of the HCR initiator complex may be contacted with each other under conditions such that they can hybridize into an initiator complex, before they are contacted with the target nucleic acid molecule. The target nucleic acid molecule may therefore be contacted with a fully-formed HCR initiator complex.

Figure 11:
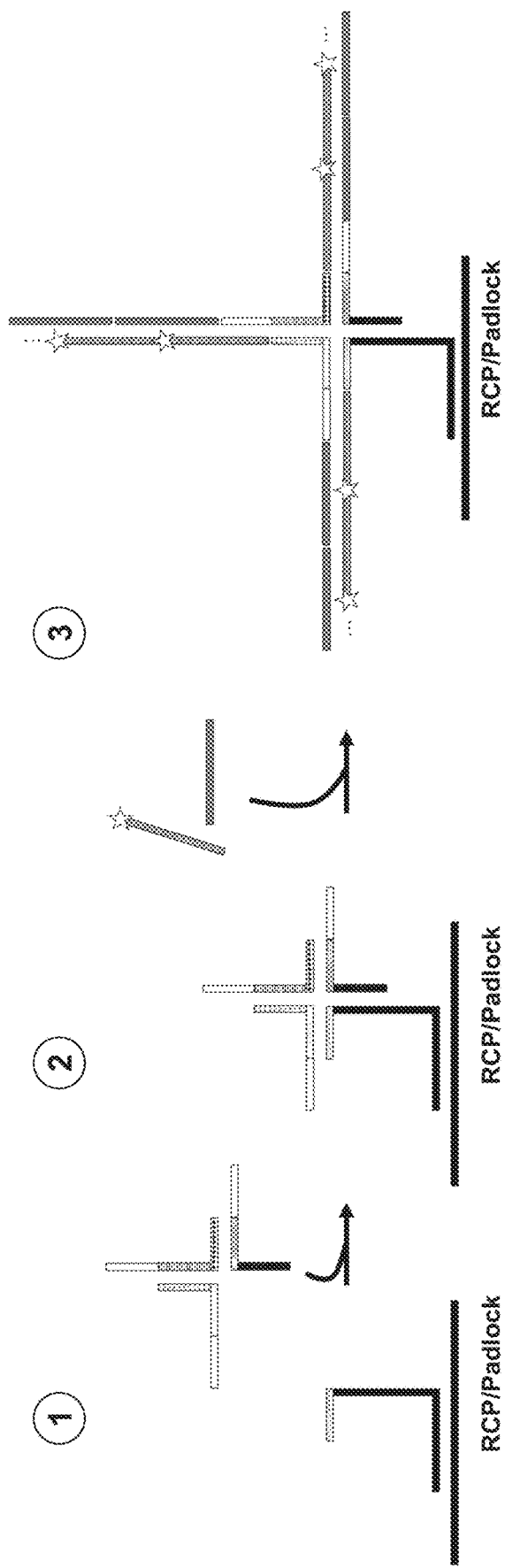
FIG. 11 shows an exemplary process for the assembly of an LO-HCR initiator complex on a target nucleic acid molecule and the generation of multiple LO-HCR products.

Alternatively, the target nucleic acid molecule may be contacted with the components of the HCR initiator complex simultaneously or sequentially. In such embodiments, the HCR initiator complex would assemble on the target nucleic acid molecule. It will be understood that the manner in which the HCR initiator complex assembles will depend on the order in which the initiator components are added. For example, in methods involving the use of the LO-HCRplus HCR initiator complex, the target nucleic acid molecule may be contacted initially with the first initiator component, such that the first initiator complex can hybridize to the marker sequence. The three additional initiator components may be contacted with each other, before they are contacted with the target nucleic acid molecule, such that they can hybridize to each other to form an HCR initiator 'pre-complex'. This hybridization may be driven by rapidly heating and cooling a mixture of the three additional initiator components. Finally, this 'pre-complex', comprised of the three additional initiator components is contacted with the target nucleic acid molecule and first additional initiator component, such that the full HCR initiator complex can be formed at the marker sequence. This assembly process is shown in FIG. 11. It will be understood that corresponding assembly processes may be implemented with different HCR initiator complexes. In some embodiments, the target nucleic acid molecule may be contacted with all of the LO-HCRplus initiator components simultaneously, and the LO-HCRplus initiator complex may assemble on the target nucleic acid molecule.

The HCR initiator complexes discussed above comprise multiple initiator domains, each containing a sequence which is complementary to the input domain of a first HCR monomer. In some embodiments, each initiator domain in a given HCR initiator complex contains a sequence which is complementary to the input domain of the same HCR monomer. In such cases, the HCR initiator complex supports multiple HCR reactions which produce the same HCR polymer product, i.e. the products of the different HCR reactions supported by a single HCR initiator complex are indistinguishable from one another. As discussed above, this will strengthen the signal associated with the target analyte in question Alternatively, in some embodiments, the initiator domains in a given HCR initiator complex may contain sequences which are not all complementary to the input domain of the same first HCR monomer. That is to say, the HCR initiator complex may be capable of supporting multiple HCR reactions, which produce different HCR products, i.e. the products from different HCR reactions initiated by the same HCR initiator complex may comprise different HCR monomers and may therefore be distinguishable from one another. This may be useful in applications in which the method is used to detect multiple target analytes in a given sample, as is discussed in more detail below. In some embodiments, each initiator domain in an HCR initiator complex may contain a sequence which is complementary to the input domain of a different first HCR monomer.

In order to prevent premature initiation of the HCR reaction, or initiation of the HCR reaction in a location independent of the target nucleic acid molecule, where the HCR initiator is a sequence capable of hybridizing to the marker sequence in the target nucleic acid molecule, the initiator may be hybridized to the target nucleic acid molecule before the HCR monomers are added. As noted above, where the target nucleic acid molecule(s) comprises multiple copies of the marker sequence, a number of copies of the HCR initiator can be hybridized to the target nucleic acid molecule(s). This is the situation, for example, where the target nucleic acid molecule is an RCP, in which case there may be at least one HCR initiator hybridized to the RCP at each repeat of the marker sequence.

In some embodiments, the method of the present invention may comprise a step of washing the target nucleic acid molecule once it has been contacted with the HCR initiator, so as to remove any unhybridized HCR initiators. This washing step may be conducted by contacting the target nucleic acid molecule with any suitable buffer, as known in the art.

Once the HCR initiators have been hybridized to the marker sequence in the target nucleic acid molecule, and any unhybridized initiator sequences have been washed away, the HCR monomers may be introduced. This ensures that the HCR reactions are localised to the target nucleic acid molecule. Depending on the method by which the target nucleic acid molecule is provided, it may be the case that the target nucleic acid molecule occupies the same locality as the target analyte. In such cases, the HCR reaction is then effectively localised to the target analyte, and thus detection of the product of the HCR reaction provides information not only about the presence of the target analyte, but also about its location. This is particularly important in applications where a target analyte is to be detected in situ, i.e. in the location where it would typically exist within the sample.

The HCR reaction of the present method may be conducted according to a so-called "stepwise" protocol. In such embodiments, the step (ii) of performing the HCR reaction may comprise; (a) contacting the target nucleic acid molecule with an HCR initiator having an output domain (initiator domain) complementary to the input domain of a first HCR monomer; (b) contacting the target nucleic acid molecule with first HCR monomers having an input domain complementary to the initiator output domain (initiator domain) and an output domain complementary to the input domain of a second HCR monomer; (c) optionally washing the target nucleic acid molecule; (d) contacting the target nucleic acid molecule with second HCR monomers having an input domain complementary to the output domain of the first HCR monomer and an output domain complementary to the input domain of the first HCR monomer; (e) optionally washing the target nucleic acid molecule; and (f) repeating steps (b) to (e) until a detectable HCR product has been generated.

It will be understood that this stepwise protocol results in the manual build-up of the HCR polymeric product by adding first and second HCR monomers in turn, until the polymer is of sufficient length to be detectable. This method is highly effective at generating a detectable HCR product.

Alternatively, the HCR reaction may be carried out using a so-called "one pot" protocol. In some embodiments, the step (ii) of performing an HCR reaction comprises a step of contacting the target nucleic acid molecule simultaneously with at least two different species of HCR monomers. According to this protocol, the target nucleic acid molecule may be contacted with, for example, a mixture comprising first and second HCR monomers. In some embodiments, the target nucleic acid molecule may be contacted with an HCR initiator before it is contacted with the at least two different species of HCR monomers. Alternatively, the target nucleic acid molecule may be contacted simultaneously with at least two different species of HCR monomers, and an HCR initiator.

This one pot method is capable of generating the HCR polymeric product more quickly than the stepwise method outlined above, as all of the components of the HCR product are present at the point at which the reaction is initiated, and the polymerisation reaction is not paused for washing steps to occur. However, although it is less time consuming, the one pot method may not in all circumstances be as efficient as the stepwise method. Accordingly, it will be understood that different protocols may be better suited to different applications, depending on whether speed or accuracy is of the primary importance, and on the target analyte, and sample etc. In a high-throughput application where the target analytes are relatively abundant, for example, the one pot protocol may be most appropriate. Conversely, for sensitive detection of a small number of target analytes present in a sample in very low concentrations, the stepwise method may be preferred. These scenarios are provided merely for exemplary purposes, and the selection of an appropriate protocol is well within the routine skill of the person skilled in the art.

In addition to the HCR reaction discussed above, which is initiated by an HCR initiator hybridizing to or contained within the marker sequence in the target nucleic acid molecule, the present method may further comprise performing a second HCR reaction, which is not analyte-specific. This may act as a positive control. Such a further HCR reaction may thus be a general, or control, reaction. This reaction is unrelated to the identity of the target analyte, but may be used to confirm that a target nucleic acid molecule (e.g. an RCP) has been generated, and/or may be useful in multiplex situations or where sequential labelling is taking place (e.g. where multiple HCR products are sequentially generated for each analyte or marker sequence), and/or in the analysis of the results, e.g. where the HCR products are detected by imaging, to align images etc. This control or general HCR reaction may be initiated via a general (e.g. common or control) sequence present in the target nucleic acid molecule (e.g. RCP). This functions in a manner akin or analogous to the marker sequence but is not analyte-specific. Thus, the general sequence is separate from the marker sequence and may be present in the target molecule (e.g. RCP) that is generated for all analytes (in other words it may be a sequence that is common to the target nucleic acid molecule provided for any analyte). Accordingly a separate general HCR initiator may be used, and this may be provided by a separate general HCR initiator molecule, which hybridizes to the general sequence in the target nucleic acid molecule or, alternatively, general HCR initiator sequence may be present within the general sequence present within the target nucleic acid molecule. The general HCR reaction also involves of a separate set of HCR monomers, which ensures that the resulting HCR product can be distinguished from any target-specific HCR products. The separate general and target-specific HCR reactions may be conducted simultaneously, or sequentially, i.e. the general HCR reaction may be conducted at the same time as, before or after the target-specific HCR reaction.

The method of the present invention may be carried out in multiplex to detect different target analytes in a given sample. Alternatively put, the method of the present invention may be used to detect multiple (i.e. 2 or more) target analytes in a given sample, wherein at least one target nucleic acid molecule is provided for each target analyte.

In certain embodiments a sample may be assayed for two or more different target analytes. In this respect, the methods of the invention are particularly advantageous for the detection of multiple analytes in a sample. For high (or higher) multiplex, a sequential method may be carried out, in which a number of analytes are detected using multiple initiators and/or HCR monomer sets, one per analyte in a first cycle of the method, and in subsequent cycles, different analytes are detected, using the same HCR monomer sets (optionally with initiators having the same initiator sequence as in the first cycle). Thus, the same monomer sets may be used in different cycles of the method, to detect different analytes. For example, for the first cycle the HCR initiators may each comprise a marker-binding sequence (marker-binding domain) specific for a different target analyte to be detected or assayed in the first cycle. Each HCR initiator used in the cycle may comprise an initiator sequence which is different from other initiators used in the cycle, and designed to initiate HCR of a different HCR monomer set. In a second or subsequent cycle, the HCR initiators may each have a different marker-binding sequence (to each other, and to the HCR initiators used in the first cycle, or in other cycles), but may have an initiator sequence common to that used in a previous or other cycle, but for each cycle the multiple HCR initiators will each be different, with a different initiator sequence. In such a sequential method, the HCR products may be stripped, or removed, from the sample, between cycles (e.g. after each cycle) for example as described in more detail below.

There is no restriction on the type of target analytes that may be detected in multiplex. Accordingly, the method may be applied in multiplex to detect multiple nucleic acid target analytes, or multiple non-nucleic acid target analytes, or a mixture of nucleic acid and non-nucleic acid target analytes. In order for multiple target analytes to be distinguished from each other, the target nucleic acid molecules that are provided in respect of each target analyte must have different marker sequences, i.e. each target analyte must be associated with a specific, distinct marker sequence. Similarly, the specific marker sequences for each target analyte in a run of the method (e.g. in a cycle of the method, or for each analyte to be detected or assayed in a sample at the same time), may in turn hybridize to separate and distinct HCR initiator sequences, such that each target analyte is also associated with a specific, distinct (e.g. unique) HCR initiator sequence, in order to initiate the polymerisation of a specific arrangement of HCR monomers, and therefore the production of a specific HCR product which may be distinguished from other HCR products. The number of different target analytes that can be detected in a given sample is therefore limited only by the ability of the detection methods available to distinguish between different HCR products, which indicate different marker sequences and therefore different target analytes.

Further, in some embodiments, multiple target nucleic acid molecules may be provided for each analyte, and these may be detected commonly as a group (i.e. they may share a common marker sequence, or in other words have the same marker sequence) or they may be detected individually (i.e. they may each have a different marker sequence). This may be of interest, for example in the detection of a nucleic acid molecule, e.g. RNA, in a manner akin to smFISH, where multiple probes are used, each hybridizing to a different target sequence in the target analyte. The probes may each provide or lead to the generation of a separate target nucleic acid molecule.

Accordingly, for multiplex methods, where more than one target nucleic acid molecule is generated, the target nucleic acid molecules may be distinguished from one another on the basis of the HCR products that are generated. This may be achieved in various ways. The marker sequence in each target nucleic acid molecule may be distinct, and may lead to the generation of a distinct HCR product, which may be distinguished from other HCR products. However, multiplexing capacity may be limited by the number of available labels or detection systems for the HCR products. To increase multiplexing capacity sequential visualisation or labelling strategies may be used. The generation of a HCR product may be viewed as the generation of a "label" or "signal" for the target nucleic acid molecule, and hence multiple HCR products may be sequentially generated for each target nucleic acid molecule, to achieve sequential "HCR labelling". Each HCR reaction may be separated by, e.g. stripping or bleaching steps to remove the preceding HCR product, or the signal therefrom. Methods of sequential visualisation reactions which may be adapted for use in the present methods are known in the art, e.g. Goransson et al., 2009 (A single molecule array for digital targeted molecular analyses. Nucleic Acids Res. 2009 January; 37(1):e7), Wahlby et al., 2002 (Sequential immunofluorescence staining and image analysis for detection of large numbers of antigens in individual cell nuclei. Cytometry, 47(1):32-41, 2002).

Combinatorial methods of labelling, e.g. ratio labelling, using different combinations and/or ratios of different labels are known in the art and may be used to increase the number of different target nucleic acid molecules and hence different target analytes which may detected at one time, or in the same reaction. For example, combinations using different coloured and/or fluorescent labels and/or different ratios of different coloured and/or fluorescent labels may be used. For example, such "colour"-coding with different combinations of coloured and/or fluorescent labels may be used in multiplex assays based on detection by flow cytometry or microscopy (e.g. by imaging). Alternatively, using lanthanide isotope labels cyToF detection may be used. By way of example, 7 different fluorophores may be grouped into 4 different types. There are 7 different combinations if labelled with only one colour, with 2 colours there are 21 different combinations, for 3 and 4 colours there are 35 different combinations and so on.

Such methods may therefore rely on generating a sequence of HCR products which may be detected to generate a sequence of signals, by means of which a target nucleic acid molecule, and hence a target analyte may be detected. In other words, each analyte is detected and distinguished by a combinatorial signal, or more particularly a combinatorial HCR "labelling" scheme.

In some representative embodiments of the invention, multiple analytes may be detected in parallel. For example for a given sample, multiple analytes may be detected at the same time, e.g. in the same reaction. In other representative embodiments of the invention, multiple analytes may be detected sequentially.

A combinatorial detection method may involve using a set of HCR initiator molecules for the marker sequence in each target nucleic acid molecule, which are used sequentially, with a cognate set of HCR monomers for each HCR initiator, and a HCR signal is detected for each HCR reaction in sequence, together to provide the distinguishing signal for that marker sequence (and hence target nucleic acid molecule). Thus whilst different HCR monomer sets may be provided with or detected by the same label, the particular combination and sequence of labels detected will identify and distinguish the particular initiator set/marker sequence. By way of example, in a first cycle, a first HCR initiator may be used which is cognate for a HCR monomer set detectable by a first label. The first HCR product may be detected, and it may then be removed from the RCP. In the second cycle a second HCR initiator may be used, having the same binding domain as the first HCR initiator but a different second domain which hybridizes to the first HCR monomer of a second HCR monomer set which is detectable by a second label, and so on in subsequent cycles, to build up a "label sequence". The number of cycles may vary depending on the degree of multiplexing required, e.g. 2, 3, 4, 5, 6, or more cycles. It will be understood that it is not necessary for each cycle to have a different label, and the same label could be used in different cycles (but not in all of the cycles); what is required is that for each marker sequence (and therefore each target nucleic acid molecule), a different sequence of labels is determined.

Thus the same marker sequence may support the generation of multiple sequential HCR products, which may be detected in sequence, together to provide a signal which identifies and distinguishes that marker sequence, and hence the target nucleic acid molecule and/or target analyte.

In such sequential labelling methods, the marker sequence present in the target nucleic acid molecule may be considered as a single continuous sequence, in the sense that it provides a single binding site for a HCR initiator. However, as a variation to this approach the marker sequence may be arranged in the form of a barcode sequence with multiple separate barcode positions which are "read" separately and sequentially, in order to detect and identify the marker sequence. In such a scheme a HCR product may be generated and detected for each barcode position, in sequence. This may be performed by a sequential HCR labelling method similar to the above, except that for each barcode sequence a set of HCR initiators will be provided which each has a different binding domain, each specific for a different barcode position.

In the present method, the step of performing an HCR reaction in order to generate a detectable HCR product may therefore comprise multiple individual HCR reactions. Accordingly, it may be seen that in different ways a single marker sequence may be capable of supporting (or initiating) multiple HCR reactions. Analogously to the above, if the HCR initiator is contained within the marker sequence in the target nucleic acid molecule, then the marker sequence may comprise multiple adjacent or sequential HCR initiator sequences, each capable of hybridizing to a different HCR monomer and therefore of initiating an independent HCR reaction.

To perform sequential HCR labelling reactions it may be desirable or in some cases necessary to remove a detected HCR product, before the next cycle is performed (i.e. before the next sequential HCR reaction is initiated). As noted above, HCR products also need to be removed in methods in which multiple analytes are detected in different cycles. There are a number of methods by which this removal can be done, which are known in the art. Such methods may include the use of high temperature and/or chemical agents, such as formamide, to denature or disrupt the hybrid between the HCR product and the target nucleic acid molecule. However, in some cases it may be desirable to use less harsh methods and displacement probes may be used, for example invading probes, which invade the hybrid between the target nucleic acid molecule (marker sequence) and the HCR initiator or first HCR monomer, in order to displace the hybridized HCR product. Various such displacement (or displacer) probes have been described, for example the so-called "eraser probes" of Xiao and Guo 2018, Front Cell Dev Biol 6:42, doi 103389/fcell 2018.00042 and Douse et al 2012, NAR 40(7) 3289-3298, which may adapted for use herein. This may include providing the HCR initiator with a separate displacer-binding toehold domain, which does not hybridize to the target nucleic acid molecule nor to a HCR initiator, and which is available for binding to a displacer probe.

In some embodiments, the first and/or second HCR monomers may comprise an overhang region (i.e. a displacer-binding toehold domain) capable of facilitating a displacement reaction to depolymerise the HCR product. This overhang region may be targeted by displacement probes. Such displacement probes comprise a sequence complementary to the overhang region, and may further comprise a sequence complementary to at least a portion of the input/output domain of the first or second HCR monomer. Accordingly, they can hybridize to the overhang region of the HCR monomers within the HCR product, with the overhang region acting as a toehold, and invade the hybrid between the first and second monomers in the polymeric HCR product, thus leading to the dissociation of the HCR product. This displacement-initiated depolymerisation method may be particularly useful in situations where the method involves the use of an HCR initiator complex capable of supporting multiple HCR reactions. In such situations, the HCR products may be too large to be effectively removed from the target nucleic acid molecule without the use of high temperatures and/or harsh chemical agents, which may damage the sample. Accordingly, breaking up the polymeric chain allows for the HCR product to be more readily removed. In some embodiments, this displacement mechanism may be combined with the use of temperature/chemical agents, as discussed above, in order to facilitate the removal of the HCR product.

In some situations, toehold-mediated displacement may not be necessary in order to displace a preceding HCR product. For example, it may be sufficient to simply rely on equilibrium kinetics, wherein unbound preceding HCR initiators and/or HCR monomers are washed away, and subsequent HCR initiator and/or HCR monomers are added in excess, such that the signal from the subsequent HCR product can be detected at sufficient strength.

Any appropriate mechanism for removing previous HCR products once they have been detected in order to allow subsequent HCR reactions to proceed may be implemented in the present method. Following the step of dehybridizing the preceding HCR products, it may be advantageous to also include a step of washing the sample so as to remove the previous HCR products from the sample.

The HCR product may be detected using any convenient protocol. The particular detection protocol may vary depending on the sensitivity desired and the application in which the method is being practiced. The polymer HCR product may be detected in a number of different ways. Any method known for the detection of nucleic acids may be used, for example based on size separation, e.g. various forms of electrophoresis, nucleic acid staining techniques, light scattering spectroscopy, such as dynamic light scattering (DLS), viscosity measurement, mass changes determined by e.g. surface plasmon resonance and spectrophotometric techniques based on detection of colorimetric or fluorescent labels etc. In this regard, the HCR product may be directly labelled by incorporating a label into it, or it may be indirectly labelled e.g. by hybridizing or otherwise binding a labelled detection probe to it. For example, a detection probe may be designed to hybridize to a particular sequence (e.g. a tag sequence, or detection sequence) present in one or more HCR monomers.

Conveniently, one or more of the HCR monomers may be labelled, e.g., fluorescently, or otherwise spectrophotometrically, or radioisotopically labelled or with any detectable label, such that the HCR product itself is directly labelled. In some embodiments, the direct labels may be incorporated into one or both (or more) of the cognate HCR monomers in a set, e.g. either the first HCR monomers, or the second HCR monomers, or all of the HCR monomers may be labelled. If only one of the species of HCR monomers is labelled, the other species of HCR monomers in a set of cognate monomers can act as unlabelled 'linkers', which facilitate the polymerisation of the labelled monomers. The labelled monomers may be seen as "detection HCR monomers" or "detection HCR oligonucleotides".

In an alternative embodiment, only a fraction of one or both or more species of the HCR monomers may be labelled, i.e. it may not be necessary for all of the HCR monomers of a given species to comprise a label. This may be useful where it is desired to reduce the cost involved, as labelled HCR monomers may be more expensive than unlabelled HCR monomers.

Moreover, it is not necessary for all of the HCR monomers within a given set of HCR monomers (e.g. the first and second HCR monomers) to have the same detectable label. Accordingly, in some embodiments, the different HCR monomer species within a given set of HCR monomers may comprise different detectable labels. Alternatively put, there may be multiple different detectable labels present within a given set of HCR monomers. In this manner, different HCR monomer sets, and hence different HCR products, may be distinguished by different combinations of labels. This may be particularly useful in multiplex applications, i.e. when assessing samples containing multiple different target analytes, where it is necessary to distinguish between multiple different HCR products.

Alternatively, the HCR monomers may be labelled, akin to conformationally selective probes such as molecular beacons, such that the signal (e.g. fluorescence) is detectable when the HCR monomers are in monomer form, but quenched when the monomers are brought into proximity with each other, i.e. when hybridized in the polymer. This may be done by labelling the HCR monomers with energy transfer labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

In an alternative embodiment, the acceptor and donor molecules for an energy transfer reaction may be provided on different monomers, which upon hybridization to one another allow a FRET-pair to form, and thus generate signal. In a still further format, the acceptor and donor molecules may be provided as described in e.g., LOCI (U.S. Pat. Nos. 5,340,716; 6,346,384), or as described in U.S. Pat. No. 8,198,031. The presence of an HCR product may therefore be determined via the use of an energy transfer reaction such as FRET.

Various dyes or stains may be used to selectively detect double stranded DNA products, e.g., via intercalation. Accordingly, the double stranded HCR product may be detected using such molecules. Representative detectable molecules include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. Alternatively, the nucleic acid stain may be or may incorporate an acridine dye, or a homo- or heterodimer thereof, such as acridine orange, acridine homodimer, ethidium-acridine heterodimer, or 9-amino-6-chloro-2-methoxyacridin, or an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). The nucleic acid stain may also be a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In embodiments in which the detection system is specific for the HCR polymer in question, as opposed to double stranded nucleic acid molecules in general, the detection system may, as noted above, include a detection probe that specifically binds to a detection sequence found in the HCR product. For example, a detection probe may be designed to hybridize to a particular sequence (e.g. a tag sequence) present in one or more HCR monomers. In some embodiments, both sets of HCR monomers may contain tag sequences, such that all of the HCR monomers present in the final HCR product can be labelled. In an alternative embodiment, only one set of HCR monomers may contain such a tag sequence.

A nucleic acid detection probe will comprise a sequence complementary to that of the tag sequence in the corresponding HCR monomer, such that it can hybridize to, and therefore label, the HCR monomer. The detection probe also comprises a detectable label. This may be either a directly or indirectly detectable label.

In this context, a directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels as are known in the art, such as those described above, may also be employed.

In certain embodiments, as described above, the HCR monomers may be labelled with "energy transfer" labels. As an alternative to labelling the HCR monomer, an energy transfer labelled detection probe e.g., oligonucleotide, may be used. Specific examples of such labelled oligonucleotide probes include the TaqMan® type probes, as described in U.S. Pat. No. 6,248,526, (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Other types of probe structures include: Scorpion probes (as described in Whitcombe et al., Nature Biotechnology (1999) 17:804-807; U.S. Pat. No. 6,326,145), Sunrise probes (as described in Nazarenko et al., Nuc. Acids Res. (1997) 25:2516-2521; U.S. Pat. No. 6,117,635), Molecular Beacons (Tyagi et al., Nature Biotechnology (1996) 14:303-308; U.S. Pat. No. 5,989,823).

The step of detecting the HCR product may comprise detecting a signal from the labelled HCR product. The method of signal detection may vary depending on the particular signal producing system which is employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample or a cell sample on a microscope slide, fluorescence may be detected using a fluorescence microscope. Conveniently, imaging may be used, and e.g. fluorescent microscopic images may be obtained and analysed, as demonstrated in the Example below. Fluorescence may be suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, data may be collected in this way at frequent intervals, for example once every 3 minutes, throughout the reaction. By monitoring the fluorescence of the reactive molecule from the sample the progress of the polymerisation reaction can be monitored in various ways.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other.

The data generated as described above can be interpreted in various ways. For example, simply the presence or absence of analyte may be determined by detecting the polymer. However, since the size of the HCR product is inversely related to the amount of target analyte in a sample, quantitative measurements may be possible. Accordingly, the concentration of analyte may be determined. This may conveniently be done by determining the average molecular weight of the HCR polymer product, which may be done using standard techniques. Standard curves and control samples may be used.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of HCR initiators and/or HCR monomers that may be employed typically ranges from about 2 to about 20 or higher, e.g., as up to 100 or higher, 1000 or higher, etc. wherein the multiple analytes in a sample may be detected in parallel or sequentially.

The method of the invention may be homogenous or heterogeneous. That is, it may be performed in solution, without a solid phase or support (i.e. without immobilisation of any reaction components) or it may be performed in an immobilised or solid phase-based format, for example where the target nucleic acid molecule is immobilised. Immobilisation of the target nucleic acid molecule may be achieved in various ways. For example in an in situ assay, the target nucleic acid molecule may be an RCP which is formed in a RCA reaction primed using a target nucleic acid analyte as the RCA primer. Alternatively, the target nucleic acid molecule may be a hybridization probe which binds directly to the target nucleic acid analyte. In both cases, the target nucleic acid molecule is attached to the target tissue sample which is itself fixed to a solid support. This may occur for example where a target nucleic acid is detected using a padlock probe. In another embodiment a target analyte may be immobilised, e.g. by use of an immobilised capture probe. Alternatively, the target nucleic acid molecule may be produced from an RCA reaction primed by a nucleic acid domain of an immunoRCA or a proximity probe, which is bound to an immobilised (or fixed) analyte target. In other embodiments, the target nucleic acid molecule itself may simply be immobilised to a solid support, such as a glass surface. Use of a heterogeneous, immobilised format allows washes to be readily performed, and hence for example allows for ready removal of unbound probes, and/or or other unreacted reaction components added, or spurious unwanted reactions, not physically attached to the surface. Thus, a heterogeneous, or solid phase-based method may readily be performed sequentially.

The various nucleic acid reaction components used in the present method, such as probes or reporter molecules which make up or generate the target nucleic acid molecule, the HCR initiator or HCR monomers, and any detection or displacer probes etc., may be made up of ribonucleotides and/or deoxyribonucleotides as well as synthetic nucleotide residues that are capable of participating in Watson-Crick type or analogous base pair interactions. Thus, the components may be DNA and/or RNA or any modification thereof e.g. PNA or other derivatives containing non-nucleotide backbones. Conveniently they may be DNA.

Various of the reaction components used in the method herein hybridize to one another and accordingly have regions, or domains, of complementarity, which allow hybridization to take place.

The term "hybridization" or "hybridizes" as used herein refers to the formation of a duplex between nucleotide sequences which are sufficiently complementary to form duplexes via Watson-Crick base pairing or any analogous base pair interactions. Two nucleotide sequences are "complementary" to one another when those molecules share base pair organization homology. Hence, a region or domain of complementarity refers to a region or domain of sequence that is capable of forming an intra- or intermolecular duplex, i.e. either a duplex within the same molecule (e.g. a hairpin structure) or a duplex with a different molecule.

"Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. In the case of the RCP and the RCA template, where the RCP is produced as a complementary copy of the template, the two sequences will generally have complete, or almost complete (depending on enzyme fidelity) complementarity in base sequence. However, for components which are designed to hybridize to one another (e.g. probes, reporter molecules, HCR initiators etc.), two sequences need not have perfect homology to be "complementary", or capable of hybridization. Usually two sequences are sufficiently complementary when at least about 85% (preferably at least about 90%, and most preferably at least about 95%) of the nucleotides share base pair organization over a defined length of the molecule. The degree of mismatch tolerated can be controlled by suitable adjustment of the hybridization conditions. Those skilled in the art of nucleic acid technology can determine duplex stability empirically considering a number of variables including, for example, the length and base pair composition of the respective molecules, ionic strength, and incidence of mismatched base pairs, following the guidance provided by the art. Thus the design of appropriate reaction components, and domains thereof, and the conditions under which they hybridize to their respective targets is well within the routine skill of the person skilled in the art.

It will be evident that the present methods of detection may be applied to any scenario where it is desired to detect, quantify and/or locate a target analyte, and particularly a number (i.e. multiplicity) of target analytes. The method may be used, for example, in in situ applications to detect or assess gene expression. In addition, the method may be applied in vitro to distinguish a set of target analytes, such as target nucleic acid molecules, for example following production of a cell extract. The target nucleic acids may be, or may be derived from, target nucleic acid molecules present in any sample under investigation.

The method provides an advantage in terms of the signal amplification afforded by the HCR reaction, resulting in strong signal intensity, particularly where multiple HCR products are generated for each target analyte. This allows highly sensitive detection of analytes, and enables, for example, the detection of rare transcripts or mutations, including in difficult, e.g. autofluorescent samples. The ability to accurately and specifically detect mutations allows the present method to be used in sequencing applications. The method allows for fast highly multiplexed detection, particularly when used with a sequential HCR labelling strategy. The method further allows the ability to detect analytes such as mRNA, and hence to image gene expression, over a wide portion of a tissue section at low magnification (e.g. ×20 objective) and is applicable to archival FFPE tissue sections and aged FFPE samples in which smFISH and other fluorescence-based detection strategies are notoriously challenging. The method may also have applicability to tissue microarrays for high throughput screening of potentially useful biomarkers. The method therefore has particular applicability for gene expression studies in tissue sample, including single cell studies.

Such features make the method a powerful tool that can be integrated in routine pathological diagnostics, i.e. the method is suited to use in clinical diagnostic laboratories. Furthermore, it may also be a useful research tool, for example to study or quantify expression levels and investigate the spatial distribution of gene expression. This may be of particular use in neuroscience, to chart the spatial morphology of genes in brain samples, or to identify cellular sub-types on the basis of gene expression patterns. The method can be used to identify the spatial location of both lowly expressed and newly predicted cellular subtypes based on the detection of a set of transcripts that specifically marks a given cell subtype due to its specificity. High-throughput spatial transcriptomic techniques, including sequential smFISH, spatial transcriptomics and MERFISH, have also been applied to map cellular diversity in human and mouse brain. However, these methods are technically challenging and still require posterior validation by lower-throughput assays such as smFISH. In this context, the present method could prove very valuable especially when samples characterized by high levels of tissue autofluorescence need to be analyzed (e.g., aged brain).

Finally, as the method allows the detection of a strong signal, the method could be applied to detect short RNAs or to discriminate between different splicing variants, which is not possible by smFISH. In summary, the method is a versatile, scalable and cost-effective method that can be used to quantify individual analytes, such as RNA molecules also in challenging FFPE samples, with broad applications ranging from research to routine diagnostics.

The invention will now be described in more detail in the following non-limiting Examples. In addition, a set of drawings is presented in which:

FIG. 1 shows a schematic of various possible target nucleic acid molecules, with HCR initiators hybridized thereto, and HCR polymeric products having been generated. On the left, the target nucleic acid molecule is a padlock probe which has hybridized to the substrate (either a target nucleic acid analyte, or a probe for a nucleic acid or non-nucleic acid target analyte) and been ligated. An HCR initiator has bound to the target nucleic acid molecule, and has initiated an HCR reaction, resulting in a polymer of first labelled HCR monomers (the label indicated by the star) and second unlabelled (or linker) HCR monomers. In the centre, the target nucleic acid molecule is an RCP, and the same HCR initiator and HCR reaction are shown. Finally, on the right, a protein target analyte is shown, with a padlock probe (or RCP) target nucleic acid molecule which has been generated as a reporter for the target analyte. Again, the same HCR initiator and HCR reaction are shown.

Figure 2:
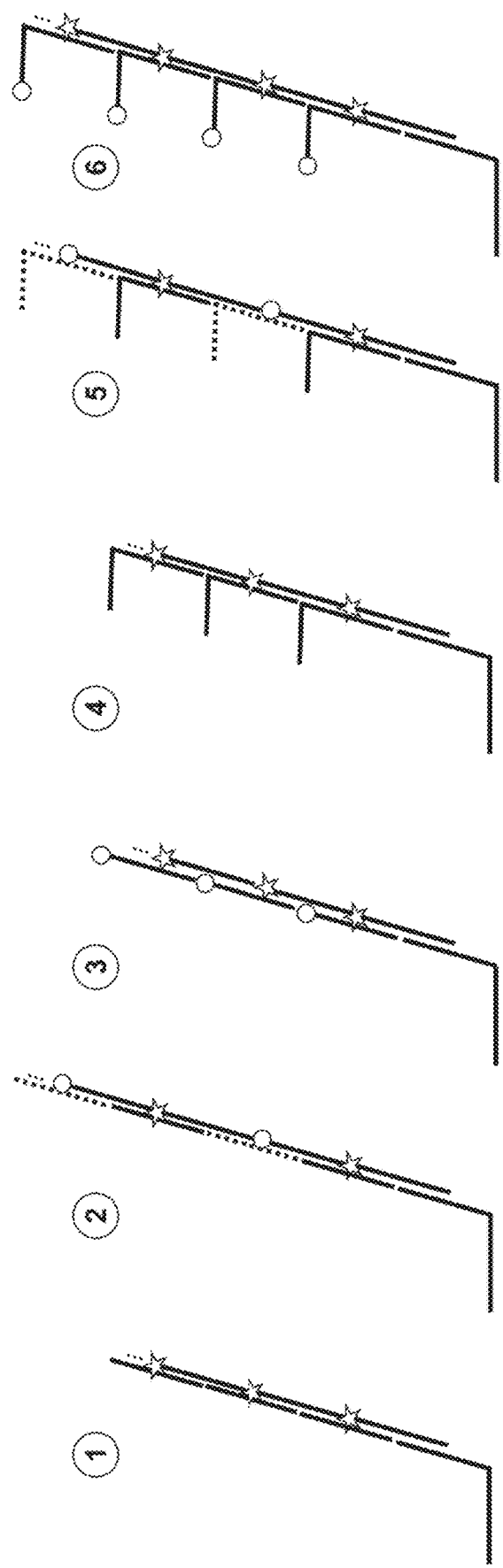
FIG. 2 shows schematics of exemplary LO-HCR polymers generated from exemplary arrangements of HCR monomers.

FIG. 2 shows schematics of HCR reactions conducted using various potential arrangements of HCR monomers. Reaction 1 is as shown in FIG. 1, with a single labelled (star) HCR monomer and a single unlabelled (linker) HCR monomer. Reaction 2 comprises two labelled HCR monomers (star and circle) and two unlabelled linker HCR monomer (block and dashed). Reaction 3 comprises two labelled HCR monomers (star and circle) which are cognate for each other, without any unlabelled linker monomers. Reactions 4 to 6 are analogous to reactions 1 to 3, but with half of the HCR monomers also having an overhang region capable of acting as a toehold to initiate a displacement reaction to depolymerise the HCR product.

Figure 3:
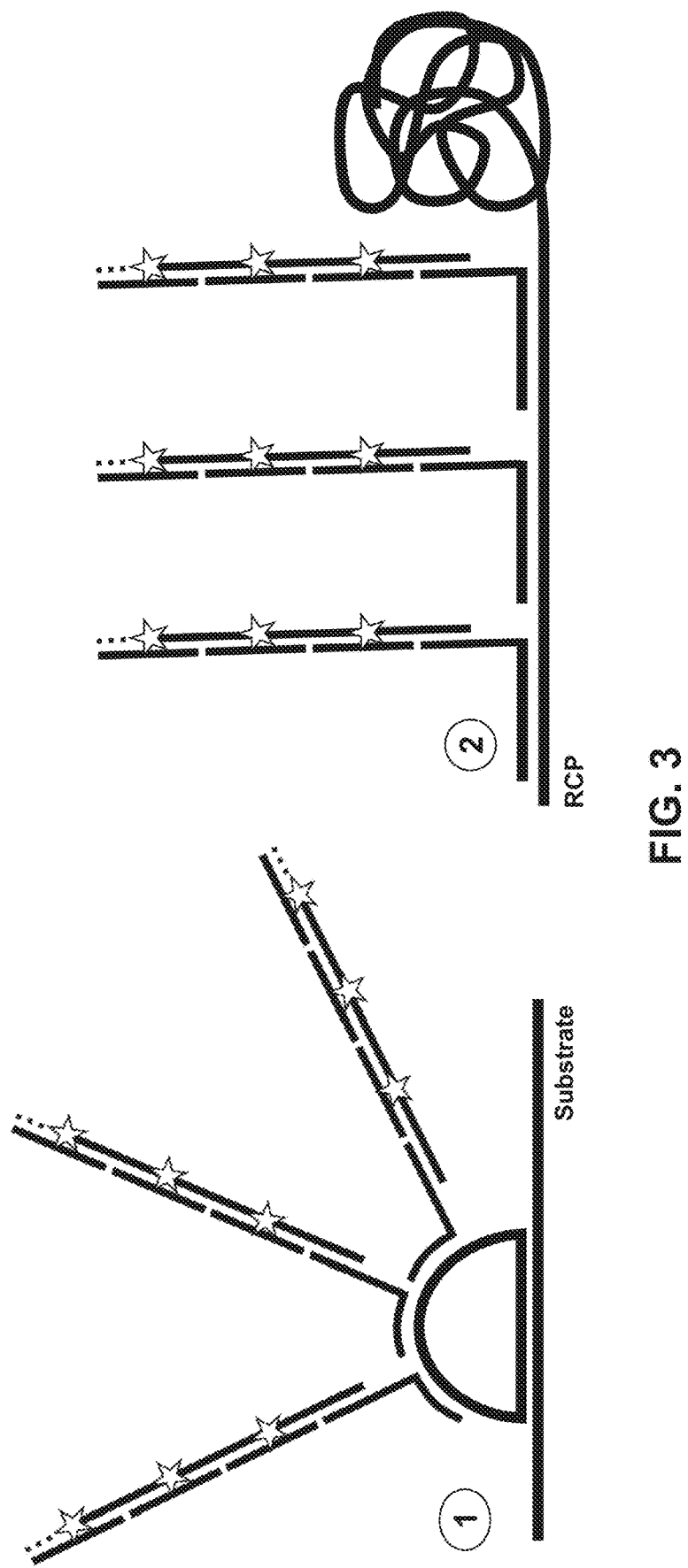
FIG. 3 shows schematics illustrating exemplary methods to increase the amplification factor.

FIG. 3 shows schematics illustrating two methods by which the amplification factor of the present method may be increased. In 1, the target nucleic acid molecule (a ligated padlock probe) comprises 3 copies of the marker sequence and has thus bound 3 HCR initiator molecules, which have in turn initiated 3 HCR reactions. The substrate may be a target analyte or a reporter molecule for the target analyte. In 2, a corresponding reaction is shown using an RCP as a target nucleic acid molecule, rather than a padlock probe.

Figure 4:
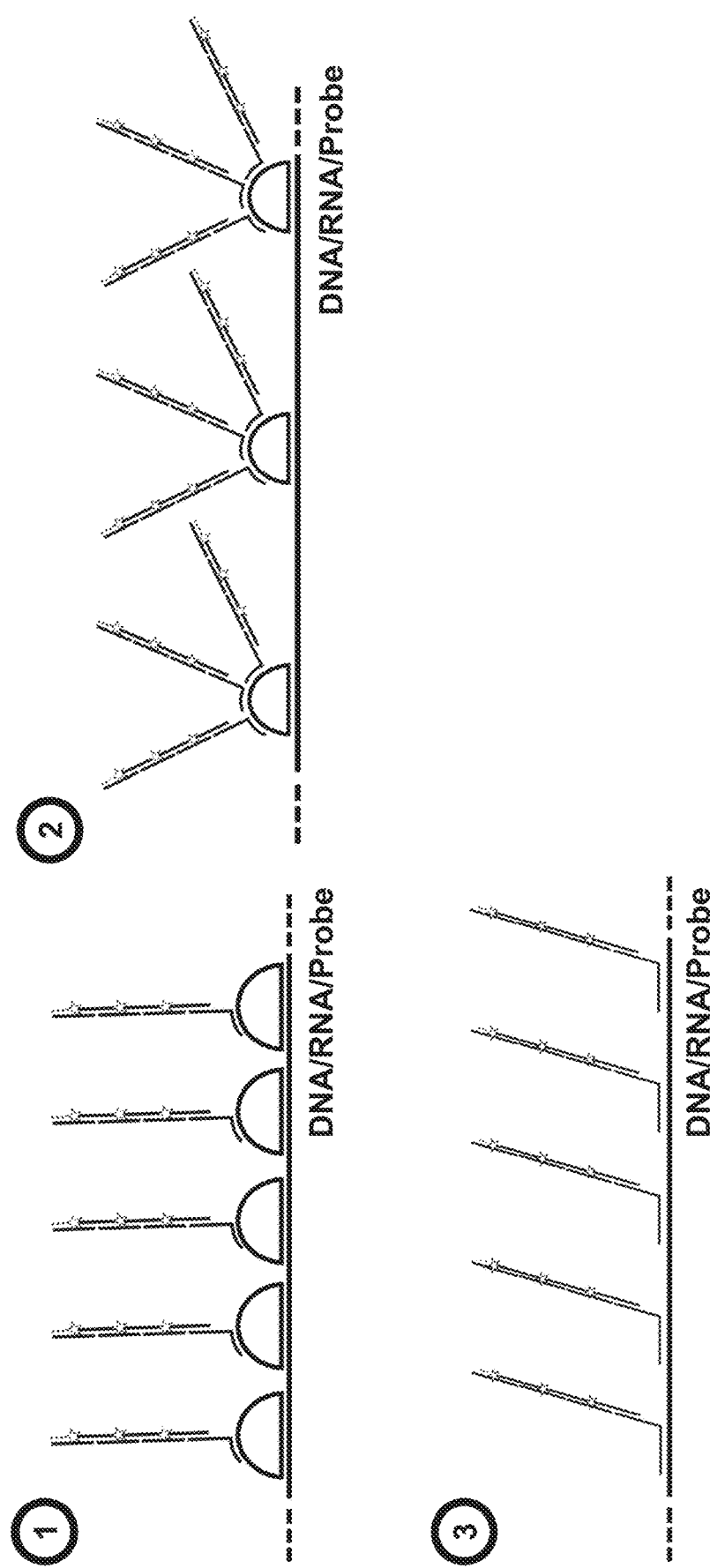
FIG. 4 shows schematics illustrating additional exemplary methods to increase the amplification factor.

FIG. 4 shows schematics illustrating further methods by which the amplification factor of the present method may be increased. In 1, multiple target nucleic acid molecules (ligated padlock probes) have hybridized to the target analyte (or DNA/RNA generated as a reporter thereof or probe for the target analyte), and thus multiple HCR reactions have been initiated from a single target analyte. Similarly, in 2, the same has occurred, but additionally each target nucleic acid molecule (ligated padlock probe) comprises multiple copies of the marker sequence, and thus two methods of signal amplification have been combined. In 3, a corresponding reaction to that of 1 is shown, wherein HCR initiators have been hybridized to multiple marker sequences present in the DNA/RNA/probe target nucleic acid molecule.

Figure 5:
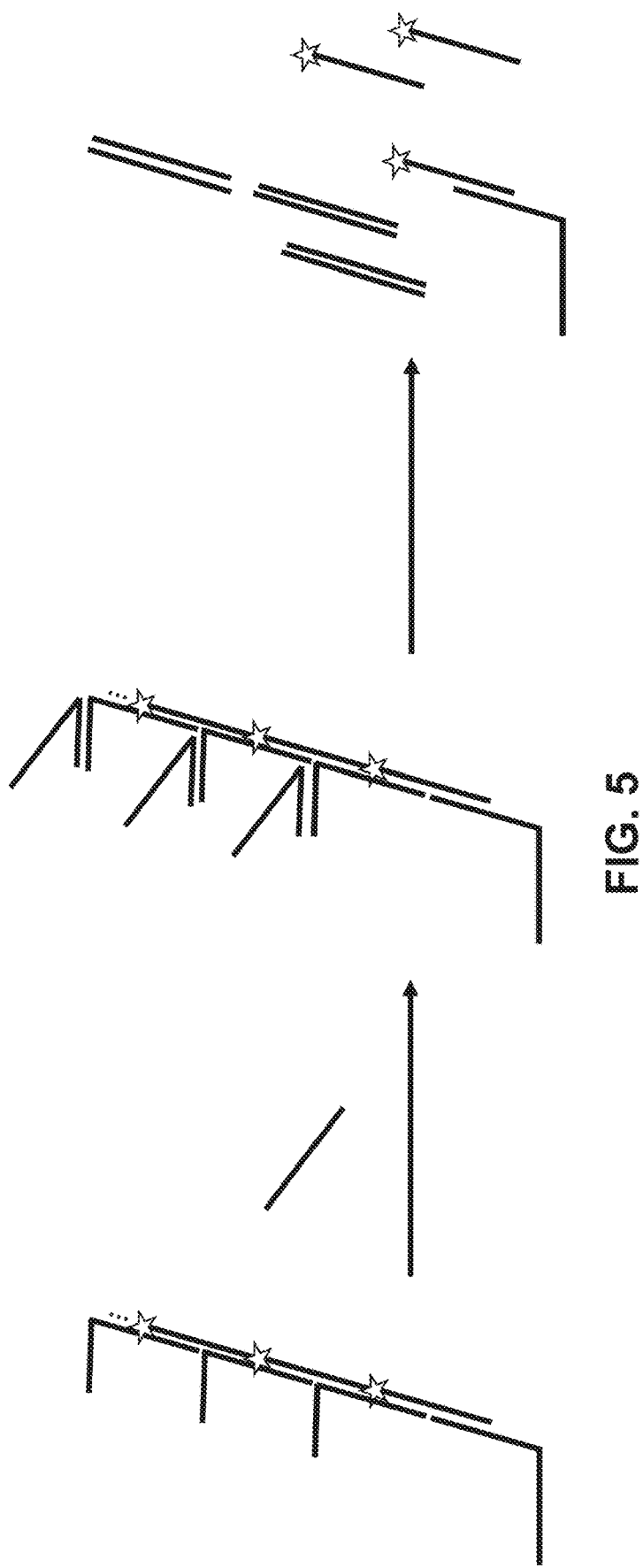
FIG. 5 shows schematics illustrating an exemplary displacement mechanism for depolymerizing a LO-HCR product.

FIG. 5 shows a schematic illustrating the displacement mechanism for depolymerising the HCR product. The displacement strands are added to the polymerised chain of the HCR product, where they hybridize to the overhang regions of the unlabelled HCR monomers, and invade and disrupt the hybrid between the first and second HCR monomers which make up the HCR product, thus resulting in displacement strand:HCR monomer hybrids.

Figure 6:
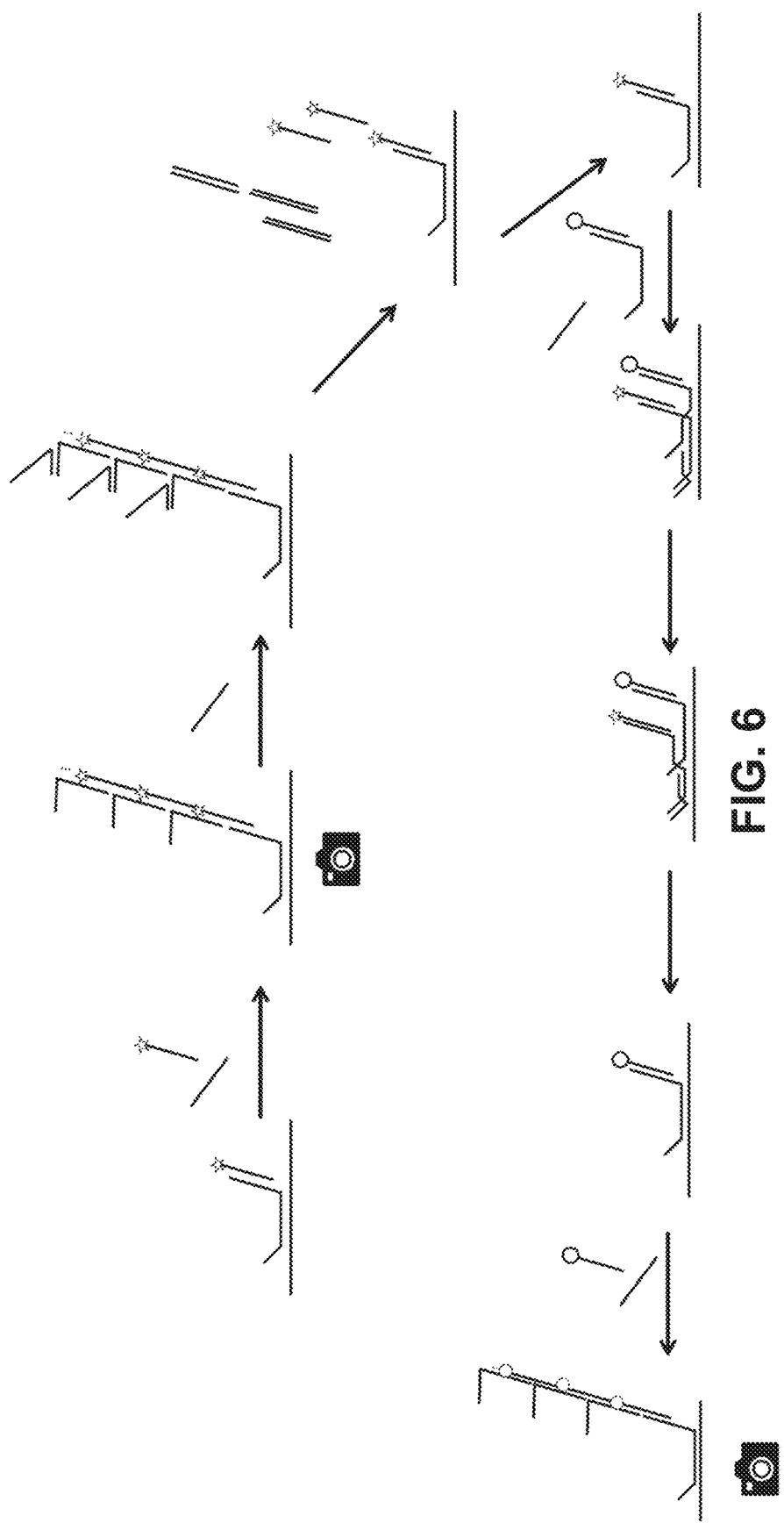
FIG. 6 shows schematics illustrating an exemplary cycle in which LO-HCR products are produced using a sequential labelling scheme.

FIG. 6 shows a schematic illustrating a full cycle of HCR products being produced in a sequential labelling scheme. The method begins with an HCR initiator complex having a displacer-binding toehold domain, a marker sequence-binding domain, and an initiator domain, bound to a target nucleic acid molecule via the marker sequence-binding domain, with a first labelled (star) HCR monomer bound to the initiator domain. Labelled and unlabelled HCR monomers are added and polymerise to form an HCR product, which is visualised (camera). Displacement probes complementary to the overhang region of the unlabelled HCR monomers are then added and, as in FIG. 5, the HCR product is depolymerised. The next HCR initiator complex is then added, together with a displacement strand complementary to the displacer-binding toehold domain of the preceding HCR initiator, and strand displacement reactions occur to disrupt the hybridization between the preceding HCR initiator complex and the target nucleic acid molecule, allowing the subsequent HCR initiator complex to bind. Finally, labelled (circle) and unlabelled HCR monomers are added and polymerise to form the subsequent HCR product, which is visualised (camera).

Figures 7A, 7B:
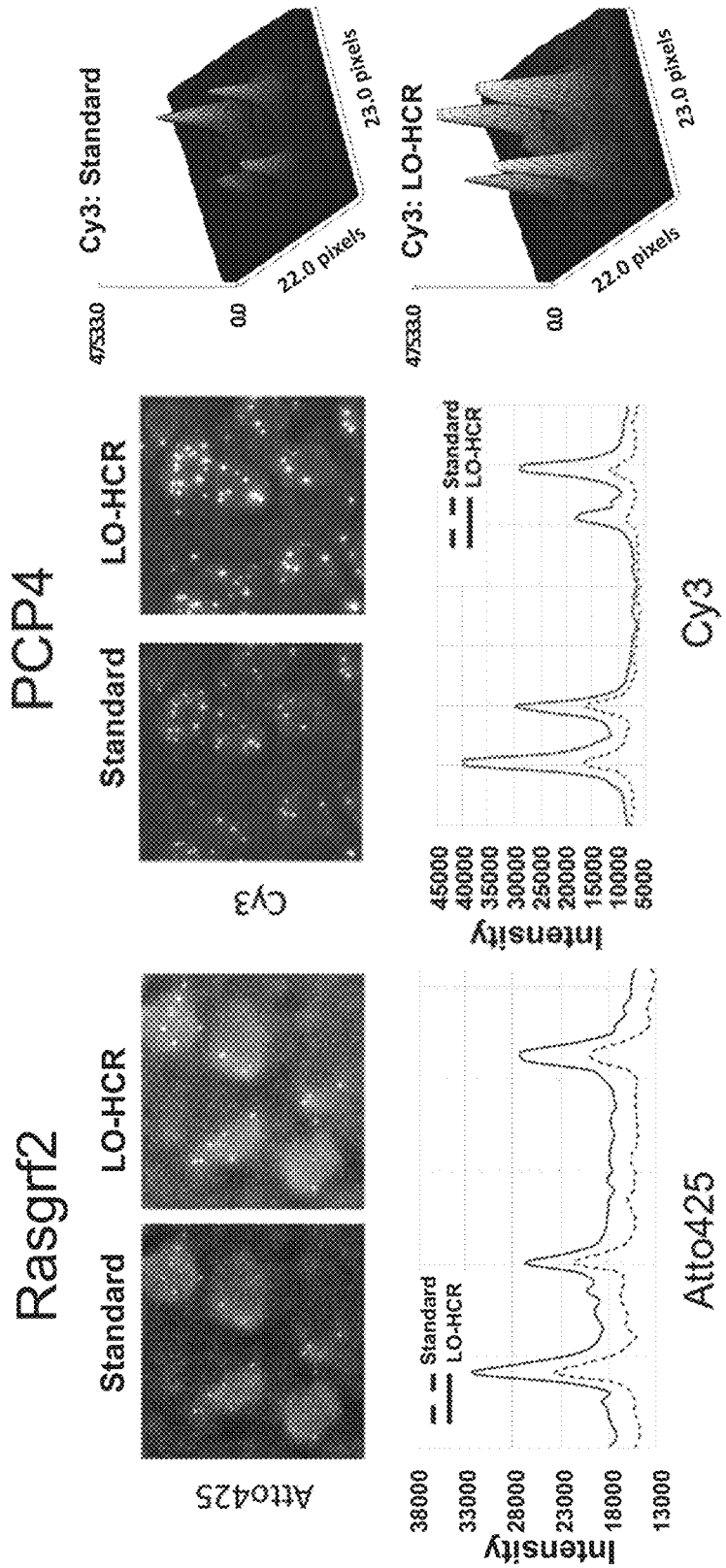
FIGS. 7A-7B show results of a mixed reaction using an exemplary stepwise LO-HCR protocol to simultaneously detect the products of two different genes, Rasgrf2 and PCP4.

FIGS. 7A-7B show the results of a mixed reaction using the stepwise HCR protocol to simultaneously detect the products of two different genes, Rasgrf2 and PCP4, using the fluorophores Atto425 and Cy3 to label the HCR products corresponding to Rasgrf2 and PCP4 target analytes, respectively. FIG. 7A shows a comparison of the fluorescence microscopy images and signal intensity plots for each gene between the LO-HCR method and a standard detection method involving a hybridization probe which hybridizes to the target nucleic acid molecule and is capable of binding a single detection oligonucleotide. FIG. 7B shows surface plots generated from a region of the fluorescence microscopy images of the same experiment, in which the brightness of the pixels in the fluorescence microscopy image corresponds to the height of the peaks in the surface plot.

Figure 8A:
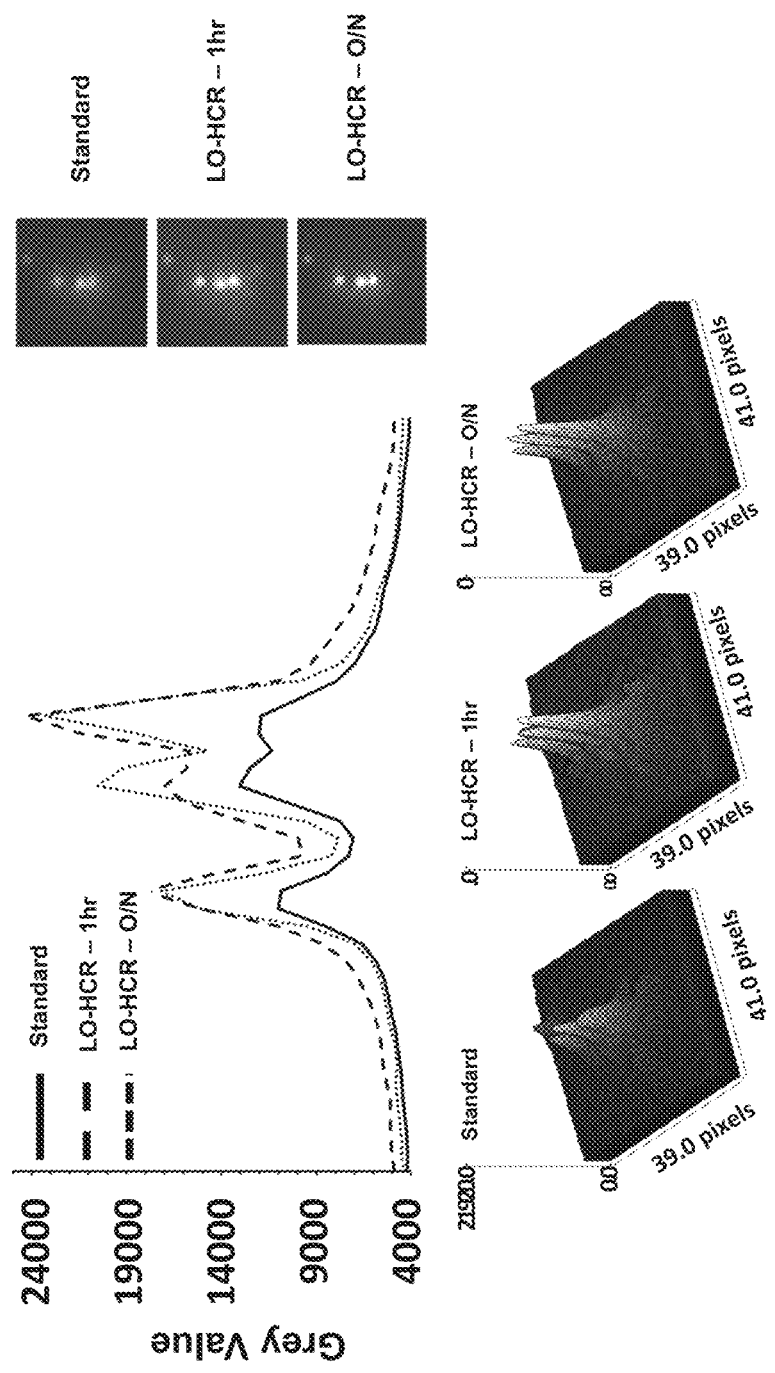
FIGS. 8A-8B show results of an exemplary one-pot LO-HCR method.
Figure 8B:
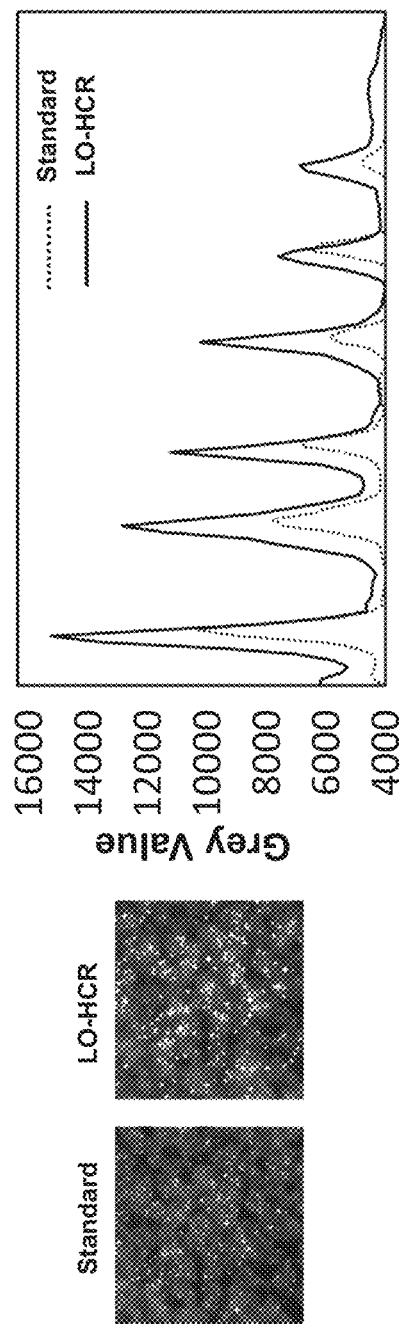

FIGS. 8A-8B show the results of an experiment to detect an mRNA target analyte using the same standard detection method, and a one pot LO-HCR method with varying incubation periods. Reverse transcriptase was used to generate a cDNA complement of the mRNA target analyte, before a padlock probe was bound to the cDNA and circularised, and an RCA reaction was carried out to produce an RCP which acted as the target nucleic acid molecule. In FIG. 8A results are shown for the standard method; a one pot LO-HCR method in which the reaction was incubated for 1 hour; and an equivalent one pot LO-HCR method in which the reaction was incubated overnight (O/N). In FIG. 8B results are shown for the standard method and for a one pot LO-HCR method in which the reaction was incubated for 30 minutes.

Figure 9:
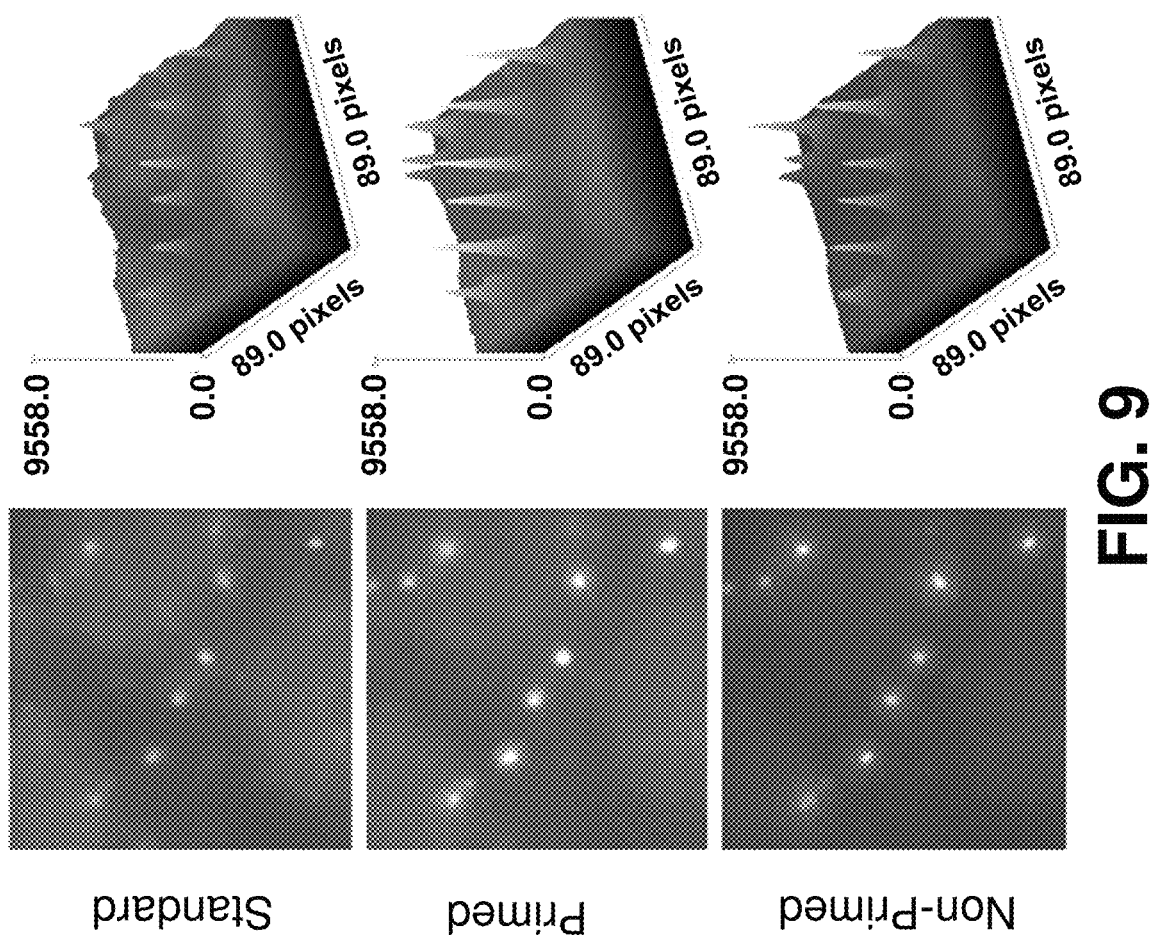
FIG. 9 shows results of another exemplary one-pot LO-HCR method.
Figure 9:
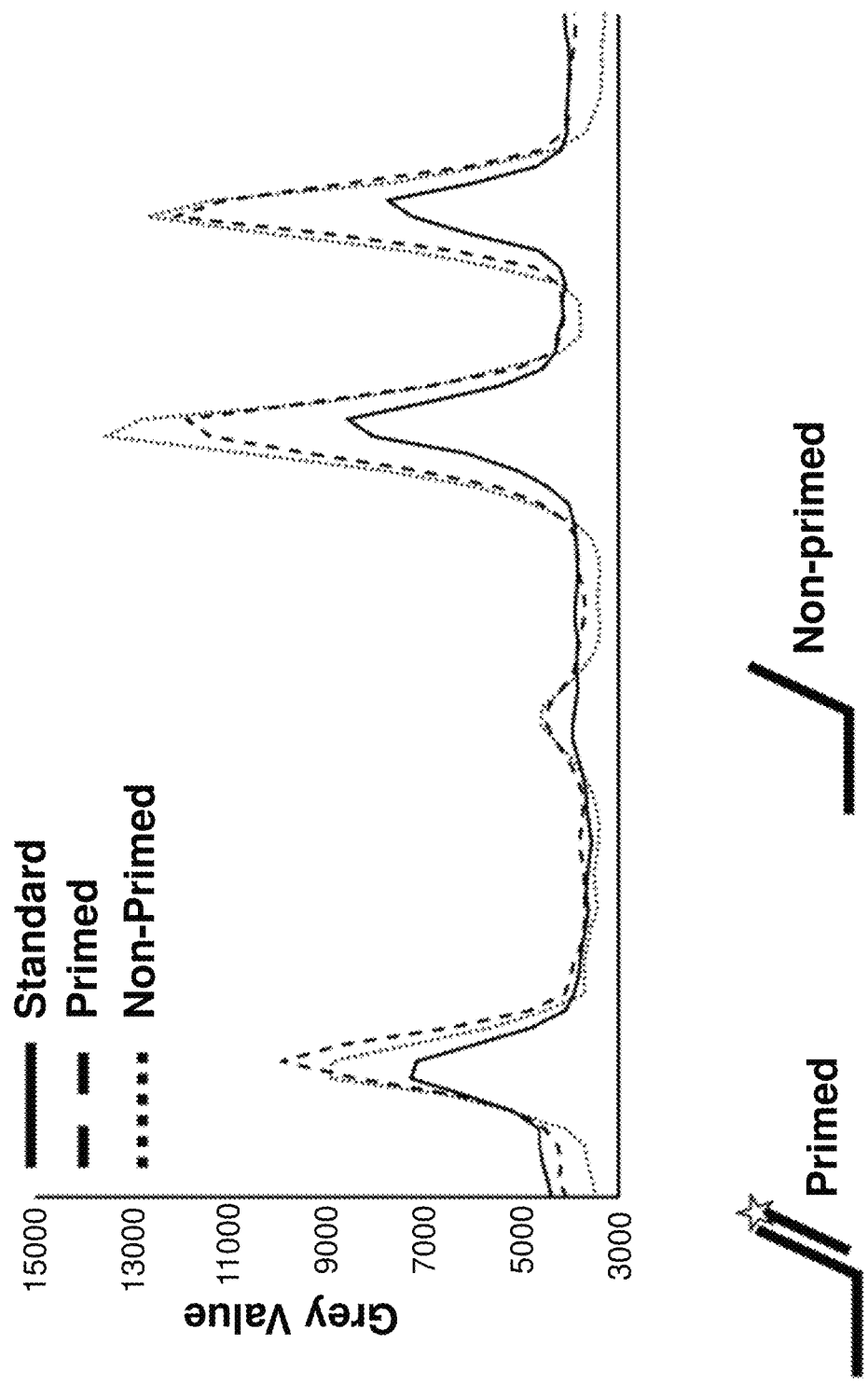

FIG. 9 shows the results of a further experiment comparing one pot LO-HCR to the standard detection method, where the LO-HCR reaction is conducted with either a primer HCR initiator complex (i.e. an HCR initiator having a first HCR monomer pre-bound) or a non-primed HCR initiator.

FIG. 10 shows a schematic of the LO-HCRplus initiator complex. 1, 2, 3, and 4 correspond to the first, second, third and fourth initiator components, respectively. The lengths of the various domains in nucleotides are indicated.

FIG. 11 shows a schematic of a possible process for the assembly of the LO-HCRplus initiator complex on a target nucleic acid molecule and the generation of multiple HCR products from a single marker sequence. In 1, the first initiator component is hybridized to the target nucleic acid molecule at the marker sequence. In 2, the pre-complex of the second, third and fourth initiator components is added and hybridizes to the first initiator component. In 3, labelled and unlabelled HCR monomers are added and polymerise into 3 separate HCR products.

V. Terminology

Specific terminology is used throughout this disclosure to explain various aspects of the apparatus, systems, methods, and compositions that are described.

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(vi) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vii) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(viii) Primer Extension

A "primer extension" refers to any method where two nucleic acid sequences become linked (e.g., hybridized) by an overlap of complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(ix) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(x) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xi) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ Thermo-Script™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xii) Label, Detectable Label, and Optical Label

The terms "detectable label" and "label" are used interchangeably herein to refer to a directly or indirectly detectable moiety that is associated with (e.g., conjugated to) a molecule to be detected, e.g., a probe for in situ assay, or analyte. The detectable label can be directly detectable by itself (e.g., radioisotope labels or optical labels such as fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature. For example, detectably labeled features can include a fluorescent, a colorimetric, or a chemiluminescent label attached to an analyte, probe, or bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore.

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and—methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLE

The following example is included for illustrative purposes only and is not intended to limit the scope of the present disclosure.

Example 1: LO-HCR Reactions on RCPs Generated from Mouse Tissue Sections

Methods
Mouse Tissue Section Preparation

Mouse strain C57BL/6 at 30 days age (P30) was euthanized and the olfactory bulb was dissected via cryosectioning. Cryosectioning was performed on ThermoFisher cryostat, at 10 μm thickness. Sections were then adhered onto ThermoFisher Superfrost glass slides and stored at −70 C until processing.
RCA Generation In Situ
Fixation and Permeabilization The tissue slide was removed from −70° C. storage and allowed to thaw for 5 min at room temperature (RT). Fixation was then performed by incubating the slides in 3.7% PFA in 1×DEPC-PBS at RT for 5 min. The slide was then washed in 1λ DEPC-PBS for 1 min at RT. This ensures that the PFA is completely removed before moving to the permeabilization step. The tissue sections were then permeabilized using 0.1M HCl in DEPC-H$_2$O for 1 min at RT and subsequently quickly washed twice in 1×DEPC-PBS.

Following this, the slides were then dehydrated with an ethanol series in 70% and 100% ethanol for 2 min respectively before the slides are air-dried for 5 min at RT. A Secure Seal Chamber (Grace Bio Labs) are applied to each section and the sections are rehydrated with 1×DEPC-PBS-T before continuing with the reverse transcription step.
Reverse Transcription Using CARTANA's Neurokit, 43.75 μl Reaction Mix (RM1), 1.25 μl of Enzyme 1 (RNase Inhibitor) and 5.00 μl of Enzyme 2 (Reverse Transcriptase) was added to each secure seal chamber and the samples were incubated in a humidity chamber at 37° C. overnight.
Probe Ligation The reverse transcription was removed from the secure seal chambers and the slides were subjected to a post-fixation step using 3.7% PFA in DEPC-PBS for 30 min at RT. After the post-fixation step, the sections were quickly washed twice with DEPC-PBS-T. Using CARTANA's Neurokit, 36.0 μl Reaction Mix 2 (RM2), 4.0 μl of Enzyme 3 (RNase H), 5.0 μl of Enzyme 4 (Tth Ligase) and 100 nM of each padlock probe were added into each secure seal chamber and incubated at 37° C. for 30 min followed by a second incubation at 45° C. for 60 min. The ligation reaction mix was then removed from the secure seal chambers and the chambers were then washed twice with DEPC-PBS-T.
Rolling Circle Amplification Using CARTANA's Neurokit, 43.0 μl of Reaction Mix 3 (RM3) and 5 μl of Enzyme 5 (129 Polymerase) was added to the secure seal chambers and incubated at either 37° C. for 3 hrs or at 30° C. overnight. This was followed by the removal of the amplification reaction mix washed twice with DEPC-PBS-T. The secure seal chambers were then removed and the slides were then dehydrated with an ethanol series in 70% and 100% ethanol for 2 min respectively before the slides were air-dried for 5 min at RT.
Initiator Hybridization The sections were rehydrated with 2×SSC and the HCR initiator mix was added at 100 nM in basic hybridization buffer (2.5×SSC+20% Formamide) and incubated at 1 hr at 20-37° C. The sections were then washed twice with basic washing buffer (2×SSC in DEPC-H$_2$O).
HCR Monomer Hybridization After the probe hybridization, the tissue section was washed with basic washing buffer. After washing, a 100 nM HCR monomer mix was added in basic hybridization buffer and allowed to hybridize for 30-60 min at 20-37° C.
LO-HCR Chain Reaction
Stepwise LO-HCR A primed HCR initiator complex comprising a labelled first HCR monomer bound to an HCR initiator was used to initiate the LO-HCR reaction. The first HCR monomer mix, comprising 100 nM labelled first HCR monomer ("detection HCR oligonucleotide") in LO-HCR hybridization buffer (2.5×SSC+5% Formamide), was added to the tissue section and incubated at room temperature for 5 min. The first HCR monomer was then removed and the second HCR monomer mix, comprising 100 nM unlabelled second HCR monomer ("linker") in LO-HCR hybridization buffer, was added and incubated for 5 min at room temperature. The second HCR monomer mixture was removed, and the first HCR monomer mix was added again and incubated for 5 min, etc. The first and second HCR monomer mixes were incubated for 10 cycles in total. The sections were then washed twice with basic washing buffer before dehydrating the sections with an ethanol series in 70% and 100% ethanol for 2 min respectively before the slides are air-dried for 5 min at RT. 10 μM SlowFade Gold antifade reagent (Invitrogen) was then added to each section and covered with a coverslip. The slide was subjected to microscope imaging.

One-Pot LO-HCR

As with the stepwise LO-HCR, a primed HCR initiator complex comprising a labelled HCR monomer bound to an HCR initiator was used to initiate the LO-HCR. An HCR monomer mix, comprising 100 nM labelled first HCR monomer+100 nM unlabelled second HCR monomer in hybridization buffer (2.5×SSC, 10% Dextran sulfate and 20% Formamide) was added to the section and incubated for 1 hr at 37° C.

The sections were then washed twice with basic washing buffer before dehydrating the sections with an ethanol series in 70% and 100% ethanol for 2 min respectively before the slides are air-dried for 5 min at RT. 10 µl SlowFade Gold antifade reagent (Invitrogen) was then added to each section and covered with a coverslip. The slide was subjected to microscope imaging.

Standard Probe/Detection Oligonucleotide Approach

Probe Hybridization

The sections were rehydrated with 2×SSC and the hybridization probe mix was added at 100 nM in basic hybridization buffer (2.5×SSC+20% Formamide) and incubated at 1 hr at 20-37° C. The sections were then washed twice with basic washing buffer (2×SSC in DEPC-$H_2O$).

Detection Oligo Hybridization

After the initiator hybridization, 100 nM detection oligo mix was added in basic hybridization buffer and allowed to hybridize for 30 min at 20-37° C. The sections were then washed twice with basic washing buffer before dehydrating the sections with an ethanol series in 70% and 100% ethanol for 2 min respectively before the slides were air-dried for 5 min at RT. 10 µl SlowFade Gold antifade reagent (Invitrogen) was then added to each section and covered with a coverslip. The slide was subjected to microscope imaging.

Results

Stepwise LO-HCR

The stepwise build-up of the LO-HCR chain was performed using a primed HCR initiator complex comprising an HCR initiator having a 20 bp marker sequence-binding site and 14 bp initiator domain, and a first labelled HCR monomer as an initiation site. The data in FIG. 7A show the results of the mixed reaction targeting RasGRF2 (using Atto425 as detection label) and PCP4 (using Cy3 as a detection label). For the RasGRF2 genes, which were visualised in the Atto425 channel, this LO-HCR method resulted in a 1.5-fold increase in signal compared to a standard 1 probe/1 detection oligo approach. The same reaction for PCP4 resulted in a 2-3 fold change in RCP intensity compared to the standard approach. This is further highlighted by the surface plot shown in FIG. 7B. It should be noted that in the Atto425 channel, the overall background was increased compared to the standard which could be due to non-specific binding of the initiator. This increase in background fluorescence was not found in the Cy3 channel. Overall, building up of the LO-HCR chain in a stepwise manner by alternately adding the first and second HCR monomers was found to result in an overall increase of the RCP intensity, while keeping the background fluorescence low.

One Pot LO-HCR

In the one-pot LO-HCR reaction, both the first and second HCR monomers were added together, so the LO-HCR chain was able to form in the tissue section while hybridizing to the initiator. Again, a primer HCR initiator complex comprising an initiator and a bound labelled HCR monomer was used. As a proof-of-concept experiment, several different conditions were investigated, including varying concentrations of first and second HCR monomers and varying incubation times. The first condition that was tested used a 100 nM concentration for both the first and second HCR monomers, and this reaction was incubated for 1 hr. A second condition was tested using 10 nM concentration for the first and second HCR monomers, and an overnight (O/N) incubation. The results of these experiments are shown in FIG. 8A. It was found that both conditions generated similar levels of fluorescence intensities over the standard 1-probe-1-detection oligo approach. It was also noted that the overnight LO-HCR using 10 nM concentration of first and second HCR monomers produced sharper signals than the first condition (1 hr using 100 nM first/second HCR monomers). A further reaction was performed using a 100 nM first and second HCR monomer mix, and an incubation time of 30 min. This was found to also provide a reasonable increase in the signal intensity compared to the standard approach. The results of this experiment are shown in FIG. 8B.

Another one pot experiment, the results of which are shown in FIG. 9, was designed to investigate whether there was a need to use a primed HCR initiator complex (i.e. an initiator with a labelled first HCR monomer bound), or whether an HCR initiator alone, i.e. non-primed, was sufficient to initiate the LO-HCR reaction. The concentration used for both the first and second HCR monomers was 100 nM, and the reaction time was 30 min at 37° C. It was found that there was very little difference in the intensities of the primed and non-primed conditions, although both conditions were found to show an increase in the signal compared to the standard 1-probe-1-detection oligo approach. It was noted, however, that the RCPs observed in the "primed" condition appear sharper compared to those RCPs seen in the non-primed condition. The conclusion drawn from this was that the "primed" condition may be considered preferable based on the sharpness of the RCPs, although when considering the signal intensity alone, both primed and non-primed conditions were equal.

The invention claimed is:

1. A method of detecting a nucleic acid in a sample, wherein the sample is a permeabilized cell sample or a permeabilized tissue sample, comprising:
   (a) contacting the sample with a circularizable probe that binds to the nucleic acid in the sample, producing a circularized probe by circularizing the circularizable probe bound to the nucleic acid, and generating a rolling circle amplification product (RCP) from the circularized probe, wherein the RCP comprises a marker sequence that identifies the nucleic acid;
   (b) after step (a), contacting the sample with (i) an initiator comprising one or more parts and (ii) a plurality of linear oligo hybridization chain reaction (LO-HCR) monomers comprising a first species and a second species, wherein at least a fraction of the plurality of LO-HCR monomers are labelled with a detectable label,
   wherein the initiator hybridizes directly or indirectly to the marker sequence in the RCP and comprises an output domain,
   wherein the first species and the second species are linear, single-stranded nucleic acid molecules and do not comprise a hairpin structure or stem-loop structure,
   wherein each of the first species and the second species comprise an input domain and an output domain,
   wherein the input domain of the first species is complementary to the output domain of the initiator and the output domain of the second species, and the output domain of the first species is complementary to the input domain of the second species;

(c) generating a polymeric LO-HCR product comprising the detectable label using the initiator and the plurality of LO-HCR monomers, wherein the polymeric LO-HCR product comprises a plurality of the first species and a plurality of the second species; and (d) detecting the polymeric LO-HCR product comprising the detectable label in the sample, thereby detecting the nucleic acid in the sample.

2. The method of claim 1, wherein the plurality of LO-HCR monomers do not comprise a repeating sequence having more than about 5, about 10, or about 20 nucleotides in length.

3. The method of claim 1, wherein the nucleic acid is a cellular nucleic acid molecule.

4. The method of claim 1, wherein the nucleic acid is a genomic DNA, a cDNA generated by reverse transcripted of an mRNA prior to step (a), an mRNA, an miRNA, or an lncRNA.

5. The method of claim 1, wherein the sample is the permeabilized tissue sample and fixed on a solid support, and the nucleic acid is detected in situ.

6. The method of claim 1, wherein step (c) comprises:
(i) contacting the RCP with the initiator and forming a hybridized complex comprising the initiator and the RCP,
(ii) adding the first species to the hybridized complex,
(iii) adding the second species to the hybridized complex, and
(iv) repeating steps (ii) to (iii) for one or more times, wherein the first species hybridizes to the initiator and the second species in the polymeric LO-HCR product.

7. The method of claim 1, wherein the method further comprises generating multiple sequential LO-HCR products by repeating steps (b) to (c) using identically or differentially labelled LO-HCR monomers.

8. The method of claim 1, wherein the nucleic acid is an RNA molecule.

9. The method of claim 1, wherein the nucleic acid is detected in the permeabilized cell sample or the permeabilized tissue sample, wherein the permeabilized cell sample or the tissue sample is fixed on a solid support.

10. The method of claim 1, wherein step (b) comprises contacting the sample simultaneously with the first species and the second species.

11. The method of claim 1, wherein step (b) comprises contacting the sample with the first species and subsequently contacting the sample with the second species.

12. The method of claim 1, wherein the initiator is pre-bound to the first species before step (b).

13. The method of claim 1, wherein step (b) comprises: (i) forming a complex comprising the initiator and the marker sequence in the RCP by contacting the sample with the initiator with the marker sequence in the RCP, (ii) washing the sample to remove the initiator not on the complex, and (iii) contacting the sample with the first species and second species after step (ii).

* * * * *